(12) United States Patent
Minami

(10) Patent No.: US 10,754,979 B2
(45) Date of Patent: Aug. 25, 2020

(54) INFORMATION MANAGEMENT TERMINAL DEVICE

(71) Applicant: MIRUWS Co., Ltd., Sapporo-shi, Hokkaido (JP)

(72) Inventor: Shigenobu Minami, Sapporo (JP)

(73) Assignee: MIRUWS CO., LTD, Hokkaido (JP)

( * ) Notice: Subject to any disclaimer, the term of this patent is extended or adjusted under 35 U.S.C. 154(b) by 215 days.

(21) Appl. No.: 15/901,327

(22) Filed: Feb. 21, 2018

(65) Prior Publication Data

US 2018/0268164 A1 Sep. 20, 2018

(30) Foreign Application Priority Data

Mar. 17, 2017 (JP) ................................ 2017-053383
Dec. 27, 2017 (JP) ................................ 2017-251060

(51) Int. Cl.
*G06F 21/52* (2013.01)
*G06F 21/62* (2013.01)
(Continued)

(52) U.S. Cl.
CPC ...... *G06F 21/6245* (2013.01); *G06F 16/2365* (2019.01); *G06F 21/10* (2013.01);
(Continued)

(58) Field of Classification Search
CPC .. G06F 21/6245; G06F 21/2365; G06F 21/10; G06F 21/105; G06F 21/64; G06F 21/78; G06F 2221/0713; G16H 10/60
See application file for complete search history.

(56) References Cited

U.S. PATENT DOCUMENTS

2004/0236788 A1* 11/2004 Sato ................... G11B 20/0084
2005/0102236 A1   5/2005 Wary
(Continued)

FOREIGN PATENT DOCUMENTS

JP   2004-318448   11/2004
JP   2005-057769    3/2005
(Continued)

OTHER PUBLICATIONS

Extended European Search Report, European Patent Application No. 18158014, dated May 17, 2018 (4 pages).

*Primary Examiner* — Ashokkumar B Patel
*Assistant Examiner* — William B Jones
(74) *Attorney, Agent, or Firm* — Hamre, Schumann, Mueller & Larson, P.C.

(57) ABSTRACT

An information management terminal device includes a health information acquisition means, a health information storage means that stores health information and a health information passbook, and a storage medium, in which the storage medium includes a concealed region accessible only by a specific program and a normal region accessible also by programs other than the specific program, the health information acquisition means adds a date/time record as the health information passbook, the health information storage means sequentially stores the health information and the health information passbook in the normal region, and that the concealed region holds a data alteration detection parameter for detecting alteration of the health information and/or the health information passbook.

9 Claims, 18 Drawing Sheets

(51) Int. Cl.
  *G06F 21/10*    (2013.01)
  *G06F 16/23*    (2019.01)
  *G06F 21/78*    (2013.01)
  *G06F 21/64*    (2013.01)
  *G16H 10/60*    (2018.01)

(52) U.S. Cl.
  CPC ............ *G06F 21/105* (2013.01); *G06F 21/64* (2013.01); *G06F 21/78* (2013.01); *G06F 2221/0713* (2013.01); *G16H 10/60* (2018.01)

(56) References Cited

U.S. PATENT DOCUMENTS

| | | | |
|---|---|---|---|
| 2009/0006868 A1 | 1/2009 | Alkove et al. | |
| 2009/0033510 A1 | 2/2009 | Izumi et al. | |
| 2009/0172245 A1 | 7/2009 | Dunstan | |
| 2009/0319791 A1 | 12/2009 | Aiyoshi et al. | |
| 2011/0302662 A1 | 12/2011 | Kannari et al. | |
| 2012/0303972 A1* | 11/2012 | Kuno | H04L 9/3263 713/189 |
| 2015/0169560 A1* | 6/2015 | Yamamoto | G06F 16/11 707/609 |
| 2015/0310188 A1* | 10/2015 | Ford | H04L 63/0428 726/28 |

FOREIGN PATENT DOCUMENTS

| | | |
|---|---|---|
| JP | 2005-316836 | 11/2005 |
| JP | 2010-010824 | 1/2010 |
| JP | 2010-182332 | 8/2010 |
| JP | 2012-018662 | 1/2012 |
| JP | 2013-037715 | 2/2013 |

\* cited by examiner

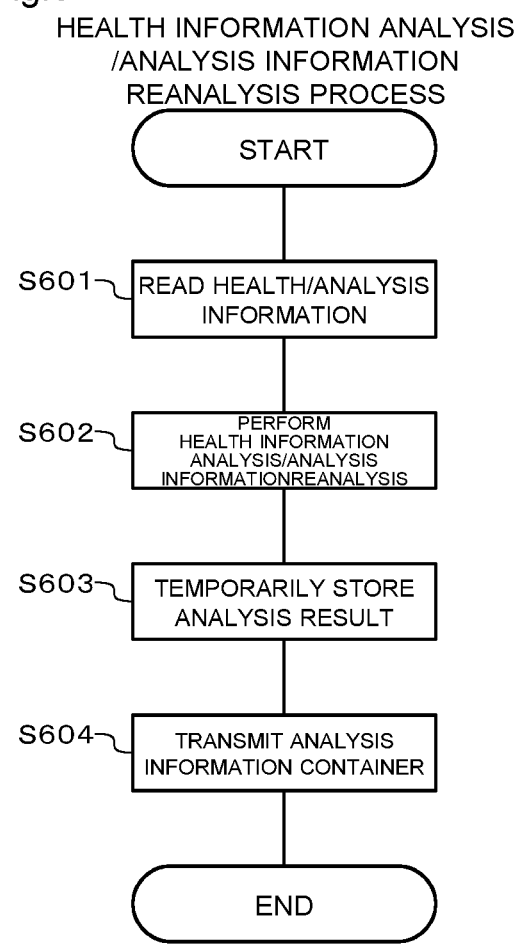

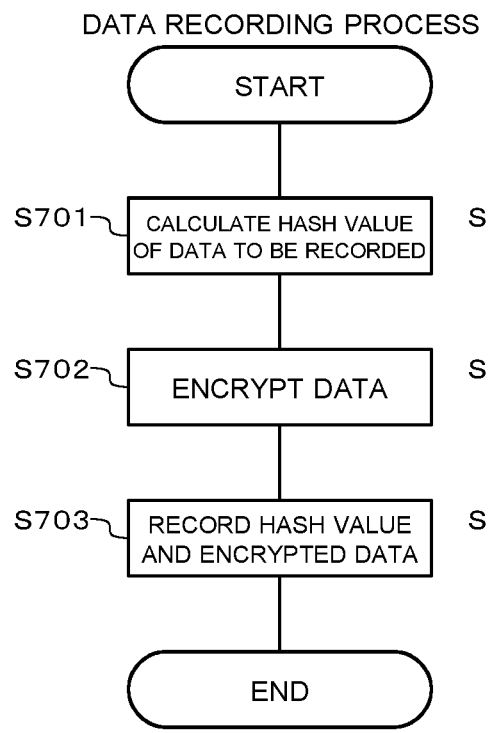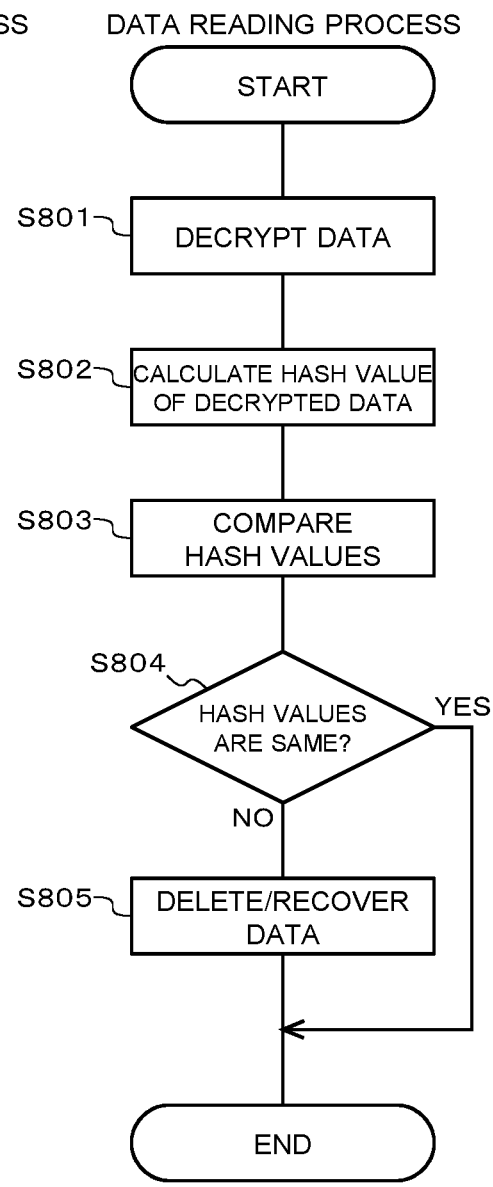

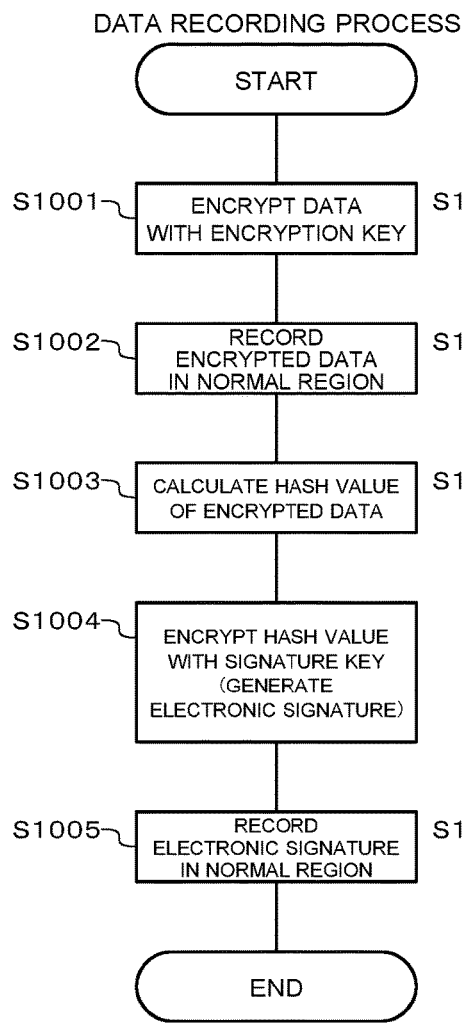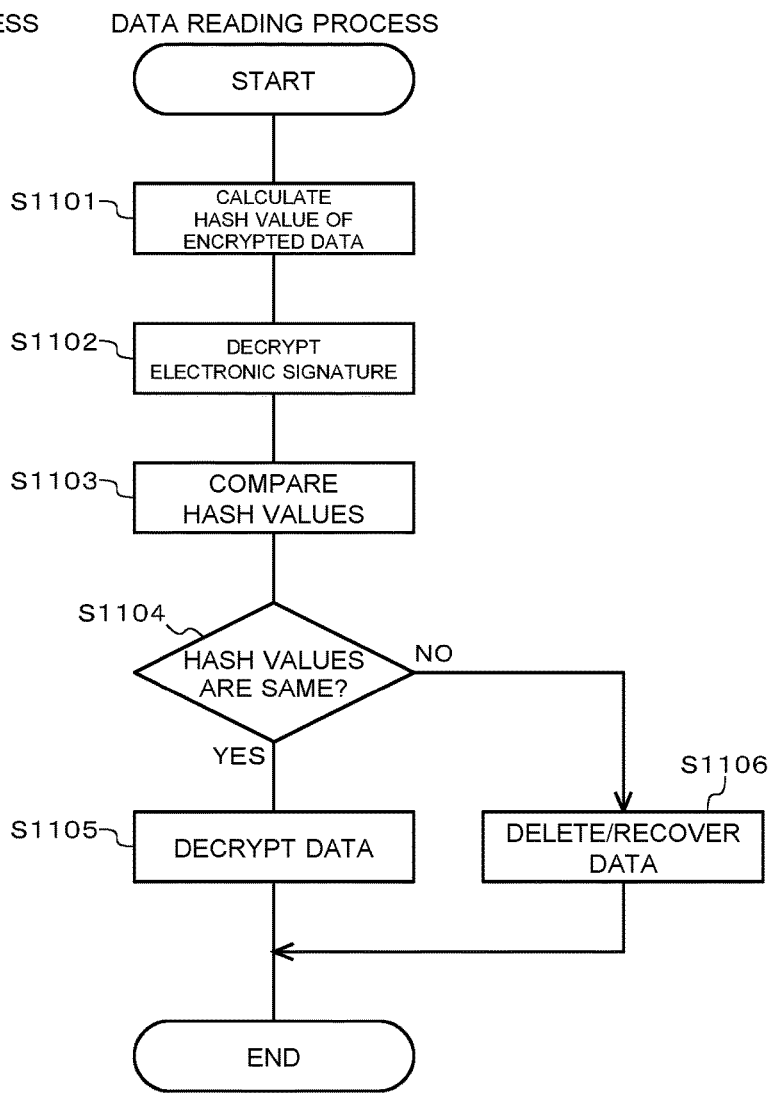
Fig.16A DATA RECORDING PROCESS
Fig.16B DATA READING PROCESS

INFORMATION MANAGEMENT TERMINAL DEVICE

BACKGROUND

Technical Field

The present invention relates to acquisition, storage, and distribution of information to be a target of information process such as data mining using artificial intelligence (AI) analysis or the like. More specifically, the present invention relates to a series of processes of acquisition, storage, distribution, analysis, visualization, and the like of information in devices and systems handling health information of persons and objects.

Related Art

In order to extract effective information from big data or the like with AI or the like, information in which the data quality, and the acquisition means and acquisition date of data are accurately recorded is required. Furthermore, regarding information related to persons, strict records and management are also required in managing and distributing data by which an individual can be specified in accordance with the Personal Information Protection Law or the like.

For example, JP 2013-37715 A discloses a portable memory device that stores content information in a hidden memory region and stores information for accessing the content information stored in the hidden memory region, in a visible region, in order to protect an authorized user from a user attempting to misuse the content.

JP 2012-18662 A discloses, in order to control use of content by a user by a method different from a conventional method, a content protection system that determines whether a user terminal has authorization to use content when the user terminal reproduces or executes the content, requests, to a license management device, license information to which the validity period is set when it is determined that the user terminal has no authorization, and determines, based on the received license information, that the user terminal has the authorization to use the content during the validity period.

JP 2010-182332 A discloses a storage device in which encryption/decryption keys are stored in a medium itself to enhance the safety and the functionality, accessing from an external device is made difficult, and only a host device having a certificate can access the key.

JP 2010-10824 A discloses, in order to access encrypted content stored in a storage device using a host controller that accesses a memory card, a copyright-protected chip including a selector that connects the host controller to a circuit in the copyright-protected chip, a register that stores an encrypted content key, decryption key generation information, and shared secret information, and a communication circuit that communicates with the host controller and transmits the encrypted content key and the decryption key generation information stored in the register to the host controller when an access means accesses content obtained by decrypting the encrypted content stored in a hard disk.

JP 2005-316836 A discloses, in order to appropriately protect content according to the use situation of the content, a content protecting system in which a content using terminal records use history information such as copying or alteration when using the content received from a content providing terminal, and transmits the information to the content providing terminal at predetermined time intervals, and the content providing terminal receives the information, determines a protection level based on the use history information, preset use conditions, and protection patterns, performs a protection process corresponding thereto, and distributes the protected content to the content using terminal.

JP 2005-57769 A discloses, in order to prevent illegal distribution of digital content, a digital content protection device that embeds a digital watermark incorporating a user's identity in digital content and provides the digital content to the user.

JP 2004-318448 A discloses, in order to prevent unauthorized copying of content at a terminal, a terminal device having a content protection function including a content reproducing means that decrypts and reproduces encrypted content using a content key included in a license acquired from a license server, and inserts user information included in the license to the reproduced content as a digital watermark.

SUMMARY

As described above, in the conventional techniques, most of the content protection targets are audio/video content with licenses, and various data of living things, behaviors, environments, equipment conditions, equipment operation, and the like, generated by persons and things which are the targets of IoT or big data are not conceived. In addition, most of conventional techniques are for content protecting by cloud-based or management server-based, and it can be said that there has been almost no technique, taking personal information protection into consideration, for individuals to determine confidentiality of data. In addition, when data acquired by various sensors such as a vital sign sensor is used as an analysis target of big data or AI, the reliability of the data is very important, but in many cases, data acquired by a sensor is transmitted to a terminal such as a smartphone by Bluetooth Low Energy (BLE) or WiFi, and then transmitted to the cloud to process the data, and attention has not been paid to alteration at the terminal particularly. Processing software, such as Android, which is often used for smartphones and tablet type terminals is relatively open, and recently security improvement such as fingerprint authentication has progressed. However, for storing personal health information having high confidentiality for a lifetime, terminals such as smartphones on which various kinds of application software are operated are not necessarily safe at present. Furthermore, when personal health information and the like are stored in a terminal, data migration in the case of changing the terminal depends on the user.

Thus, a purpose of the present invention is to provide a means for independently and securely managing information by a person or a corporation owning data (referred to as an information owner) with devices such as a smartphone, a PC, and a server.

In order to solve the above problems, an information management terminal device according to an embodiment of the present invention includes:

an information acquisition means for acquiring first information to be managed;

an information storage means for storing the first information and second information which is additional information of the first information; and a storage medium, in which the storage medium includes:

a concealed region accessible by a specific program including a program causing the information management terminal device to operate as the information storage means; and a normal region accessible also by programs other than the specific program, the information acquisition means adds a date/time record as the second information, the information storage means sequentially stores, in the normal region, the first information or a link capable of referring to the first information, and the second information or a link capable of referring to the second information, and the concealed region holds a data alteration detection parameter for detecting alteration of the first information and/or the second information.

It is thereby possible to compactly store information that can be detected when alteration of a date or content is detected at an information owner using the terminal device, and to achieve the information utilization under the control of the information owner.

In a preferred embodiment of the present invention, the data alteration detection parameter is a key for generating information for detecting whether the first information and/or the second information have/has been altered using the first information and/or the second information.

In this manner, by using a key for generating information for detecting whether data has been altered as a data alteration detection parameter, it is possible to handle a large amount of data in the case where the recordable data capacity of the concealed region is limited.

In a preferred embodiment of the present invention, the information management terminal device further includes a program alteration detection means for performing an alteration detection process of the specific program using a program alteration detection parameter for detecting alteration of the specific program, the program alteration detection parameter being included in the concealed region.

It is thereby possible to also prevent alteration of a program for acquiring and storing information, and to improve the reliability of the information dramatically.

In a preferred embodiment of the present invention, the program alteration detection means periodically performs the alteration detection process of the specific program, and the information management terminal device deletes or recovers, when the program alteration detection means detects alteration of the specific program, the first information and the second information stored from a point of time when the alteration detection process of the specific program is previously performed until a point of time when the alteration of the specific program is detected.

It is thereby possible to delete information acquired by the program that could have been altered, and to secure the reliability of the stored information. Note that, the recovery of the health information and the health information passbook in this description is achieved by storing a backup of the health information or the health information passbook in another terminal device or server device beforehand and acquiring it.

In a preferred embodiment of the present invention, the information management terminal device further includes a data alteration detection means for performing an alteration detection process of the first information and/or the second information using the data alteration detection parameter, in which the information management terminal device deletes or recovers, when the data alteration detection means detects alteration of the first information and/or the second information, the first information and the second information stored from a point of time when the alteration detection process of the first information and/or the second information is previously performed until a point of time when the alteration of the first information and/or the second information is detected.

It is thereby possible to reliably delete or recover the data that could have been altered, and to reliably eliminate data having low reliability.

In a preferred embodiment of the present invention, the information management terminal device further includes a distribution means for selecting information to be distributed from the first information and the second information stored by the information storage means and outputs the information to be distributed, in which the distribution means includes:

a concealment level setting means for setting a concealment level of the selected information to be distributed; and a means for adding the concealment level to the information to be distributed as additional information and outputting the information to be distributed.

It is thereby possible to transmit the stored information to another terminal and the like, and to actively utilize the information.

In a preferred embodiment of the present invention, the concealment level includes:

class 0 in which the information to be distributed is transmitted without being encrypted;

class 1 in which the information to be distributed is encrypted and transmitted;

class 2 in which the information to be distributed is encrypted, prohibited from being copied at an output destination, set to have a validity period, and transmitted; and class 3 in which the information to be distributed is encrypted, prohibited from being copied at an output destination, set to restrict handling of process result information generated by an arbitrary process to the information to be distributed, set to have a validity period, and transmitted.

It is thereby possible to regulate the confidentiality of the health information to be distributed, and to generate distribution information to be widely distributed to general servers like a conventional manner or for the information owner to control health information management at distribution destinations.

In a preferred embodiment of the present invention, the second information includes at least one of an output history of the distribution means, information specifying an output destination of the distribution means, the concealment level, and a process result at the output destination of the distribution means.

Accordingly, analysis, redistribution, erasure, and the like of the received health information remain as records, and it is possible to easily perform verification by the information owner who is the distribution source, and to increase the reliability of the system dramatically.

In a preferred embodiment of the present invention, the first information is information on health of a person and/or an object.

It is thereby possible to properly handle information that needs to be handled securely, such as the condition of a person's or thing's health.

An information management terminal device according to another embodiment of the present invention includes:

a reception means for receiving first information distributed from another terminal device and second information which is additional information of the first information;

an analysis means for analyzing the first information and the second information;

an output means for transmitting and/or displaying an analysis result by the analysis means to/on the other terminal device;

a storage medium; and a program alteration detection means for detecting alteration of a specific program using a program alteration detection parameter, in which the storage medium includes:

a concealed region accessible by the specific program including a program causing the information management terminal device to operate as the reception means, the analysis means, and the output means; and a normal region accessible also by programs other than the specific program, the reception means includes a concealment level determination means for determining a concealment level added to the first information and the second information, the analysis means and the output means handle the first information, the second information, and the analysis result according to the concealment level, and the concealed region includes the program alteration detection parameter for detecting alteration of the specific program.

It is thereby possible to prevent alteration of the program and to eliminate the risk of handling information and its analysis result which do not conform to the concealment level.

In a preferred embodiment of the present invention, the analysis means stores history information of the analysis or a link capable of referring to the history information of the analysis in the normal region, and the concealed region holds a data alteration detection parameter for detecting alteration of the history information.

It is thereby possible to store the history information of the analysis in a state where alteration can be detected, to easily perform verification by the information owner who is the distribution source, and to increase reliability regarding handling of the information dramatically.

In a preferred embodiment of the present invention, the information management terminal device deletes or recovers, when the analysis means detects alteration of the history information of the analysis, the history information of the analysis stored from a point of time when an alteration detection process of the history information of the analysis is previously performed until a point of time when the alteration of the history information of the analysis is detected.

It is thereby possible to reliably delete or recover the data that could have been altered, and to reliably eliminate data having low reliability.

In a preferred embodiment of the present invention, the concealment level includes:

class 0 in which the first information and the second information are handled without being encrypted;

class 1 in which the first information and the second information are encrypted and handled;

class 2 in which the first information and the second information are encrypted, prohibited from being copied at an output destination, set to have a validity period, and handled; and class 3 in which the first information and the second information are encrypted, prohibited from being copied at an output destination, set to restrict handling of the analysis result, set to have a validity period, and handled.

It is thereby possible to regulate the confidentiality of the information and its analysis result, and to generate distribution information to be widely distributed to general servers like a conventional manner or for the information owner to control health information management at distribution destinations.

In a preferred embodiment of the present invention, the reception means receives the analysis result from the other terminal device, and the analysis means reanalyzes the analysis result. It is thereby possible to perform various analyses, such as obtaining a more detailed analysis result from the analysis result and obtaining an analysis result from another viewpoint, in accordance with the concealment level, that is, according to the intention of the information owner.

In a preferred embodiment of the present invention, the first information is information on health of a person and/or an object.

It is thereby possible to properly handle information that needs to be handled securely, such as the condition of a person's or thing's health.

It is possible to compactly store, at an information owner using a terminal device, health information that can be detected when a date or content has been altered, and to achieve information utilization under the control of the information owner.

BRIEF DESCRIPTION OF DRAWINGS

FIG. 9 is a flowchart showing a health information analysis/analysis information reanalysis process in the first embodiment of the present invention;

FIGS. 10A and 10B are flowcharts showing a data recording/reading process in first embodiment of the present invention;

FIGS. 16A and 16B are flowcharts showing a data recording/reading process in the third embodiment of the present invention;

DETAILED DESCRIPTION

First Embodiment

<Configuration of Entire System Using Information Management Terminal Device>

Figure 1:
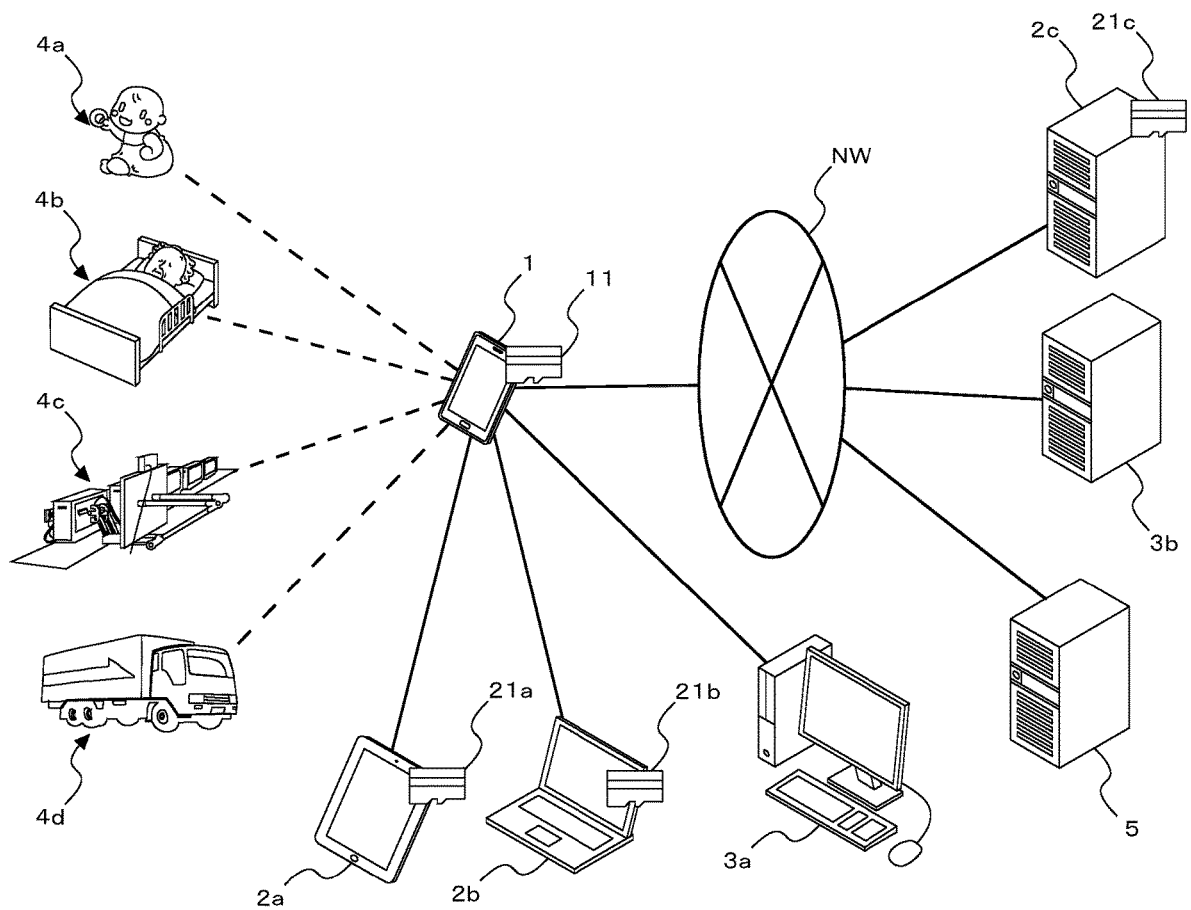
FIG. 1 is a configuration diagram of a system using an information management terminal device according to a first embodiment of the present invention.

Hereinafter, a first embodiment of the present invention will be described in detail with reference to the drawings. FIG. 1 is a configuration diagram of a system using an information management terminal device according to the present embodiment. As shown in the drawing, the information management terminal device according to the present invention is configured so that a health-information distribution side device 1 that acquires, from a sensor, and distributes information, communicates, directly or via a network NW, with health-information reception/analysis side devices 2a to 2c that receive and analyze information (hereinafter, referred to as a health-information reception/analysis side device 2 as a whole unless they especially need to be distinguished). In addition, the health-information distribution side device 1 is configured so as to communicate, directly or via the network NW, with terminal devices 3a and 3b that are not the information management terminal device according to the present embodiment but general computers and server devices (hereinafter, referred to as a terminal device 3 unless they especially need to be distinguished). Then, the health-information distribution side device 1 is configured so as to communicate wirelessly or wiredly with various sensors such as a sensor 4a attached to an infant, a sensor 4b attached to an elderly, a sensor 4c attached to a manufacturing apparatus, and a sensor 4d attached to a car, (hereinafter, referred to as a sensor 4 as a whole unless they especially need to be distinguished). In addition, the health-information distribution side device 1 and the health-information reception/analysis side device 2 are configured so as to also communicate, via the network NW, with a management server device 5 that stores information on programs operating on the devices and on the sensor 4.

The health information in the present invention is a generic term of information generated or involved by persons or objects. For example, information related to human health includes biological information (an electrocardiogram, a pulse wave, heartbeat, a pulse, body temperature, and the like), behavior information (sleep, meals, excretion, GPS positions, purchase, medication, medical history, and the like), and environmental information (temperature, humidity, atmospheric pressure, air pollution, pollen, and the like), and information generated by objects, that is, information related to object health includes equipment condition information (abnormal sound, temperature, vibration, and the like), equipment operation information (operation information on a steering wheel, an accelerator, a brake, and the like, abnormal sound information on non-destructive testing, operation times, GPS positions, persons in charge of operation, and the like), and equipment environmental information (almost the same as human). Those who handle the devices of the health-information distribution side device 1, the health-information reception/analysis side device 2, the terminal device 3, and the like are collectively referred to as users, and in particular, the user who distributes health information or the like using the health-information distribution side device 1 is referred to as an information owner.

The present invention is not limited to the health information on persons and objects as described above, and various kinds of information may be handled. For example, like in the case of storing or distributing documents, such as drawings to be attached to a contract, with the correctness secured, various kinds of information the correctness security and the alteration detection of which are required can be managed using the information management terminal device according to the present invention to manage.

Since the basis of the present invention is one-to-one communication by Peer to Peer (P2P) between the health-information distribution side device 1 and the health-information reception/analysis side device 2 or the terminal device 3, a specific cloud server or the like is not required. Naturally, connection with a cloud server is also possible as extension of P2P communication.

In the present embodiment, the health-information distribution side device 1 is implemented by using a distribution side medium 11 implemented by a recording medium, the security of which is enhanced, in combination with a smartphone, tablet, PC, or the like (referred to as a device), and the health-information reception/analysis side device 2 is implemented by using a reception/analysis side medium 21 in combination of a device. As a recording medium, for example, an SD card having the SeeQVault (registered trademark) standard can be used. In this recording medium, a concealed region and a normal public region are defined by a processor incorporated in the recording medium. Among these, only specific authentication software operating on the device can access the concealed region by using a public key generated from a secret key stored in the concealed region of the recording medium. In other words, there is a medium having a concealed region that cannot be seen from a general file system provided by an operating system (OS) installed in the device, but can only be accessed by specific authentication software. Note that, a recording medium is not limited to the SD card having the SeeQVault standard as long as the recording medium has a standard having a similar mechanism, and other recording mediums may be used.

<Configuration of Health-Information Distribution Side Device>

Figure 2:
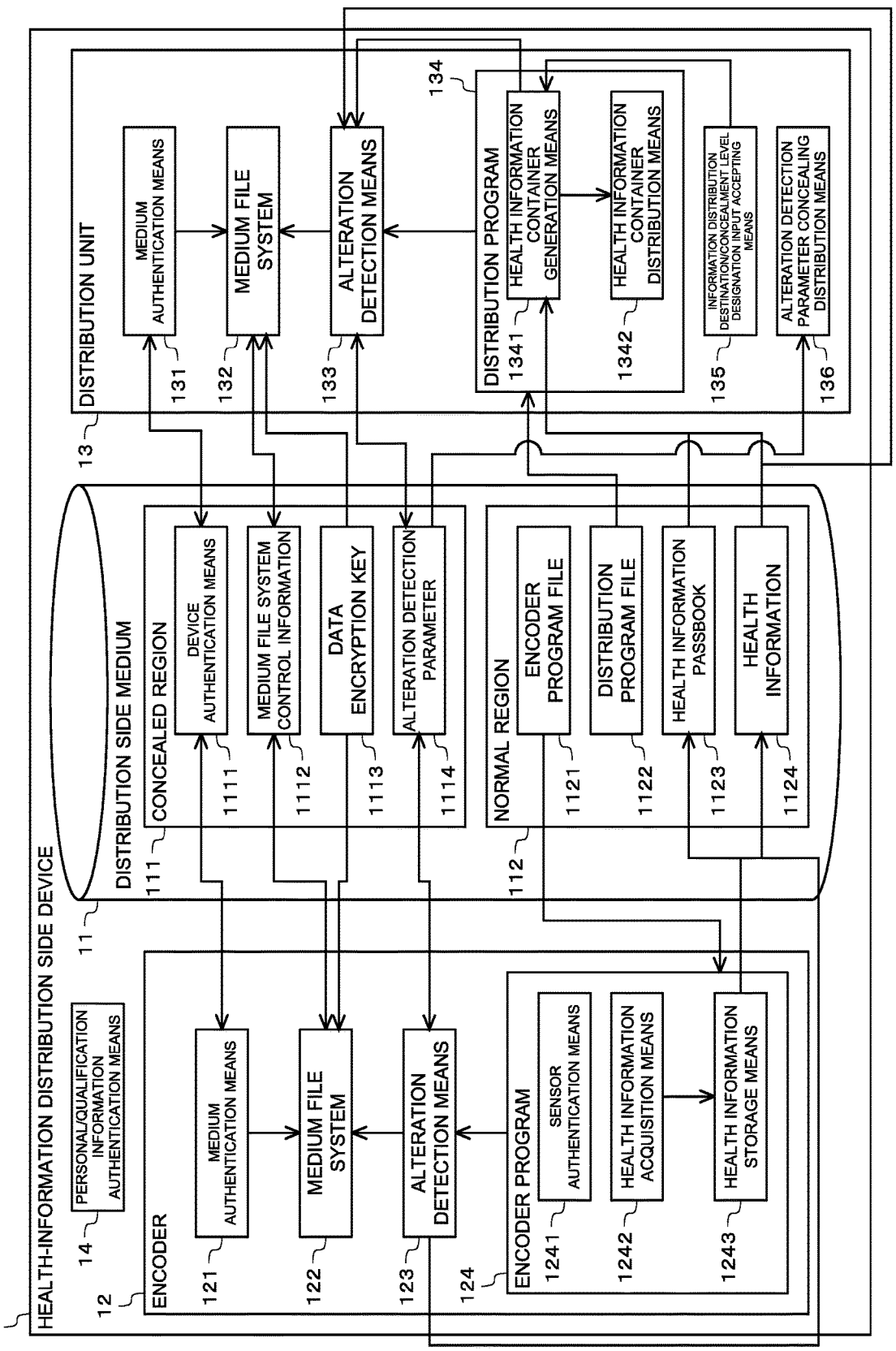
FIG. 2 is a functional block diagram of a health-information distribution side device according to the first embodiment of the present invention.

FIG. 2 shows a functional block diagram of the health-information distribution side device 1. As shown in the drawing, the health-information distribution side device 1 includes a distribution side medium 11, an encoder 12 that acquires health information from a sensor 4 and records the health information in the distribution side medium 11, a distribution unit 13 that transmits the health information to the health-information reception/analysis side device 2 or the terminal device 3, and a personal/qualification information authentication means 14 that performs authentication when the health information is acquired or distributed.

The distribution side medium 11 has a concealed region 111 and a normal region 112. As described above, the concealed region 111 can be accessed by only specific authentication software operating on the device using the public key generated from the secret key stored in the concealed region of the recording medium. Furthermore, as to be described later, the concealed region 111 can be accessed only when mutual authentication between the device and the medium, that is, between a device authentication means 1111 and a medium authentication means 121 or 131 is established. The normal region 112 is managed not by a general file system provided by the OS of the device or the like, but by a private medium file system working with medium file system control information 1112 (information on a pointer for achieving sequential writing to the medium or the like) held by the concealed region 111.

The concealed region 111 includes a device authentication means 1111 that performs mutual authentication between the distribution side medium 11 and the health-information distribution side device 1, the above medium file system control information 1112, a data encryption key 1113 that is a key for encrypting/decrypting data when the data is read from or written to the normal region 112, and an alteration detection parameter 1114 such as a hash value used to detect unauthorized alteration of a program file, a health information passbook, and health information in the health-information distribution side device 1.

The normal region 112 includes an encoder program file 1121 for receiving health information from the sensor 4 and storing the received health information, a distribution program file 1122 for distributing the stored health information to the health-information reception/analysis side device 2 or the terminal device 3, a health information passbook 1123 that is a record of circulation of the health information, and storing of health information 1124 received from the sensor 4.

Here, the health information passbook 1123 sequentially records, as attributes of the health information acquired from the sensor 4, a sensor identifier of each sensor 4, the acquisition date/time, type, and size of the health information, a data alteration detection parameter (for example, a hash value of the health information), and the like without overwriting. In addition, when health information is output from the health-information distribution side device 1 to the health-information reception/analysis side device 2 or the terminal device 3, the health information passbook 1123 contains information on the output history, the output destination, the concealment level set at the time of the outputting, the analysis result returned from the output destination, and the like.

Note that, the information included in the concealed region 111, and the encoder program file 1121 and the distribution program file 1122 which are included in the normal region 112 are recorded in the distribution side medium 11 at the time of the initial setting of the distribution side medium 11 or by a reliable distribution method.

The encoder 12 includes a medium authentication means 121 that performs mutual authentication between a device and a medium with the device authentication means 1111, a medium file system 122 for accessing the normal region 112, an encoder program 124 for acquiring health information from the sensor 4 and storing it in the health information passbook 1123 and the health information 1124, and an alteration detection means 123 that detects alteration of the health information passbook 1123, the health information 1124, and the encoder program 124.

The encoder program 124 is for the health-information distribution side device 1 to load the encoder program file 1121 from the normal region 112 and execute it, and includes a sensor authentication means 1241 that authenticates the sensor 4, a health information acquisition means 1242 that acquires health information from the sensor 4, and a health information storage means 1243 that stores the health information in the health information 1124 and stores additional information of the health information in the health information passbook 1123.

The distribution unit 13 includes, similarly to the medium authentication means 121, a medium authentication means 131 that performs mutual authentication between a device and a medium, a medium file system 132 for accessing the normal region 112, a distribution program 134 for distributing the health information passbook 1123 and the health information 1124, an alteration detection means 133 that detects alteration of the health information passbook 1123, the health information 1124, and the distribution program 134, an information distribution destination/concealment level designation input accepting means 135 that accepts a distribution destination of the health information and the health information passbook, and a concealment level to be set at the time of distribution from the information owner, and an alteration detection parameter concealing distribution means 136 that conceals and distributes the alteration detection parameter 1114.

The distribution program 134 is for the health-information distribution side device 1 to load the distribution program file 1122 from the normal region 112 and execute it, and includes a health information container generation means 1341 that containerizes the health information passbook 1123 and the health information 1124 to generate a health information container to be distributed, and a health information container distribution means 1342 that distributes the health information container to the health-information reception/analysis side device 2 or the terminal device 3.

The alteration detection parameter concealing distribution means 136 distributes the health information to another health-information reception/analysis side device 2 and the like, and then provides the concealed alteration detection parameter (a hash value or the like) of the distributed health information to verify whether alteration has been made.

In the present embodiment, the options for the concealment level, the designation of which is accepted from the information owner by the information distribution destination/concealment level designation input accepting means 135, are as shown in Table 1. The concealment level is basically designated by the information owner to a health information container to be distributed and handled as additional information when the health information is recorded or distributed. As shown in Table 1, in class 0, which has the lowest concealment level, only health information including the date of the health information that is difficult to alter remains as evidence at the information owner, and the handling of the distributed information depends on the distribution destination. In this case, it is possible to transmit information to a general terminal device (a traditional cloud service or the like) as shown as the terminal devices 3a and 3b in FIG. 1. In order to achieve the concealment level of class 1 or higher, an analysis side that receives the information container also needs a secure storage medium. By installing reception/analysis software that is difficult to alter in this medium, it is possible to make it difficult to freely distribute the received container. In addition, a history such as redistribution is written and recorded in the health information passbooks on the receiving side and the information owner side. Specifically, in the case of the designation of class 1, the received health information needs to be decrypted. The key for the decryption needs to be contained in the concealed region of the receiving side beforehand. In class 2, the information owner can further designate the control such as the prohibition of redistribution, validity period, and erasure of the received health information. In class 3, a similar designation can be applied to the analysis result.

212 can be used similarly to the distribution side medium 11. The concealed region 211 includes a device authentication means 2111, a medium file system control information 2112, a data encryption key 2113, and an alteration detection parameter 2114 which are similar to the concealed region 111.

TABLE 1

| CONCEALMENT LEVEL | ENCODER | | DECODER | |
|---|---|---|---|---|
| | MEDIUM | FUNCTION | MEDIUM | FUNCTION |
| CLASS 0 (NO ENCRYPTION) | NEEDED | STORING ALTERATION-PREVENTIVE HEALTH INFORMATION | NOT NEEDED | (DEPEND ON FUNCTION OF SERVER) |
| CLASS 1 (ENCRYPTION OF ORIGINAL DATA) | NEEDED | ENCRYPTING AND STORING ALTERATION-PREVENTIVE HEALTH INFORMATION ALTERATION | NEEDED | DECRYPTING RECEIVED DATA |
| CLASS 2 (ENCRYPTION AND CONTROL OF COPYING OF ORIGINAL DATA) | NEEDED | PROHIBITING COPYING OF ORIGINAL DATA AT TRANSFERRED DESTINATION/SETTING EXPIRATION DATE | NEEDED | PROHIBITING RECEIVED ORIGINAL DATA/ERASING EXPIRATION DATE |
| CLASS 3 (ENCRYPTION AND CONTROL OF COPYING/DELETION OF ORIGINAL DATA, CONTROL OF COPYING/DELETION OF PROCESS RESULT) | NEEDED | PROHIBITING COPYING OF ORIGINAL DATA AT TRANSFERRED DESTINATION/SETTING EXPIRATION DATE, CONTROLLING ANALYSIS PROCESSING RESULT | NEEDED | PROHIBITING RECEIVED ORIGINAL DATA/ERASING EXPIRATION DATE, PROTECTING ALTERATION OF AUTHENTICATION PROCESSING SOFTWARE, CONTROLLING TRANSFER OF PROCESS RESULT |

In the present embodiment, it has been described that the encoder 12 includes the medium authentication means 121, the medium file system 122, and the alteration detection means 123, and the distribution unit 13 includes the medium authentication means 131, the medium file system 132, and the alteration detection means 133, but these functions may be shared. However, in either case, the medium authentication means 121 and 131, the medium file systems 122 and 132, and the alteration detection means 123 and 133 are tamper-resistant (obfuscation of software codes), and the software (core software) is essential to access the concealed region 111.

<Configuration of Health-Information Reception/Analysis Side Device>

Figure 3:
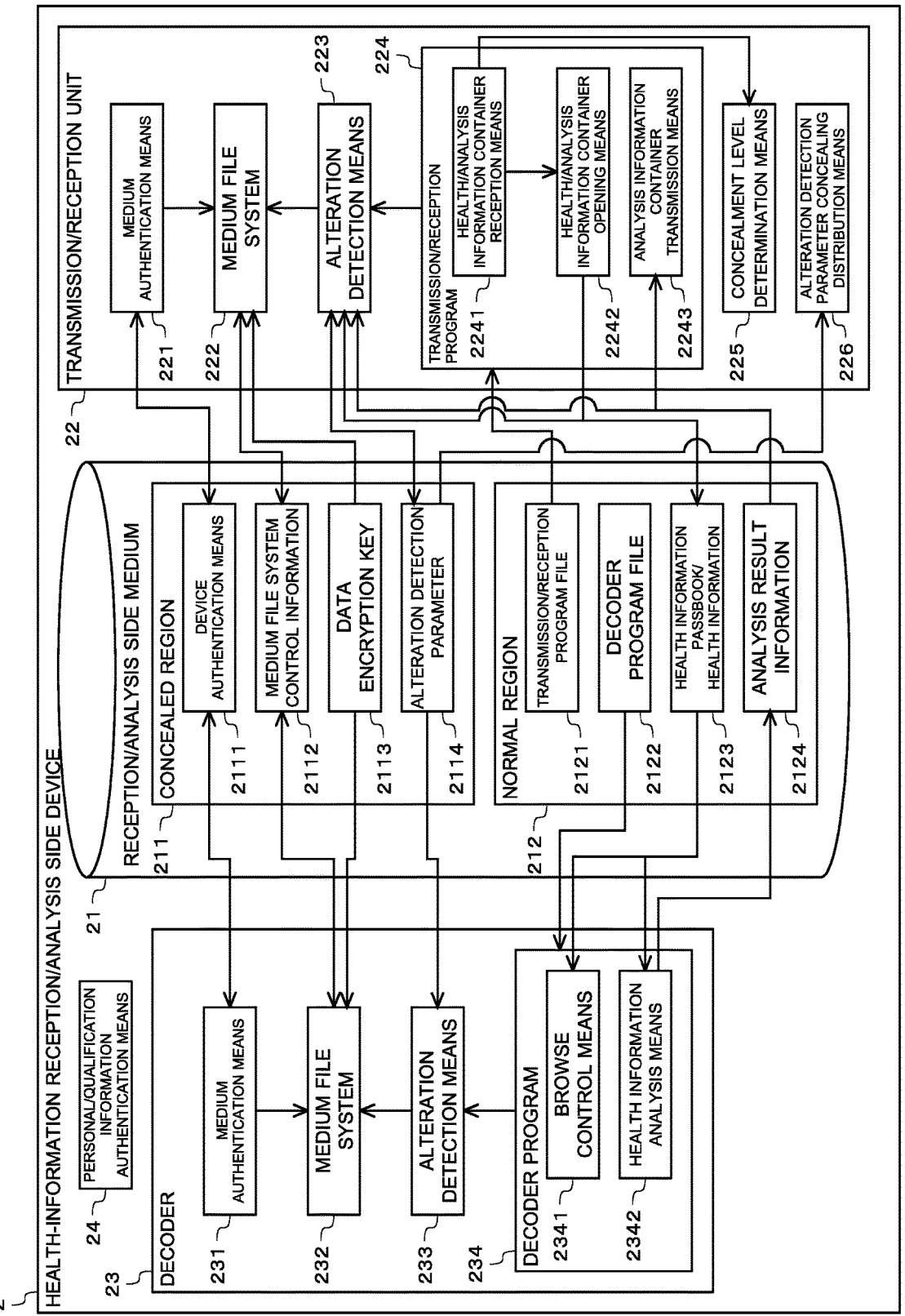
FIG. 3 is a functional block diagram of a health-information reception/analysis side device according to the first embodiment of the present invention.

FIG. 3 shows a functional block diagram of the health-information reception/analysis side device 2. As shown in the drawing, the health-information reception/analysis side device 2 includes a reception/analysis side medium 21, a transmission/reception unit 22 that receives health information from the health-information distribution side device 1, transmits the analysis result to the health-information distribution side device 1, transmits a request of reanalysis of the analysis result of the health information to another health-information reception/analysis side device 2 or terminal device 3, receives the reanalysis result, and the like, a decoder 23 that controls browsing and analyzes the received health information, and a personal/qualification information authentication means 24 that performs authentication when the health information is received, browsed, or the like.

As the reception/analysis side medium 21, a recording medium having a concealed region 211 and a normal region The normal region 212 includes a transmission/reception program file 2121 for receiving health information from the health-information distribution side device 1 and transmitting the analysis result of the health information to the health-information distribution side device 1, another health-information reception/analysis side device 2, terminal device 3, or the like, a decoder program file 2122 for analyzing and controlling browsing the received health information, health information passbook/health information 2123 for storing the health information and the information added thereto, and analysis result information 2124 for storing the analysis result of the health information and the like.

Note that, the information included in the concealed region 211, and the transmission/reception program file 2121 and the decoder program file 2122 which are included in the normal region 212 are recorded in the reception/analysis side medium 21 at the time of the initial setting of the reception/analysis side medium 21 or by a reliable distribution method.

The transmission/reception unit 22 includes a medium authentication means 221 that performs mutual authentication between a device and a medium with the device authentication means 2111, a medium file system 222 for accessing the normal region 212, an alteration detection means 223 that detects alteration of the medium file system 222, the health information passbook/health information 2123, the analysis result information 2124, and the like, a transmission/reception program 224 for receiving and opening a health information container or an analysis information container, and transmitting the analysis result of the health information by the decoder 23 as an analysis information container, a concealment level determination means 225 that determines the concealment level set to the health information container or the analysis information container, and an alteration detection parameter concealing distribution means 226 that conceals and distributes the alteration detection parameter 2114.

The transmission/reception program 224 is for the health-information reception/analysis side device 2 to load the transmission/reception program file 2121 from the normal region 212 and execute it, and includes a health/analysis information container reception means 2241 that receives the health information container from the health-information distribution side device 1 and receives the analysis information container from another health-information reception/analysis side device 2 or terminal device 3, a health/analysis information container opening means 2242 that opens the received health information container or analysis information container and records the information to the health information passbook/health information 2123, and an analysis information container transmission means 2243 that distributes the analysis result of the health information by the decoder 23 stored in the analysis result information 2124 as an analysis information container.

The alteration detection parameter concealing distribution means 226 distributes the analysis result of the health information to the health-information distribution side device 1, another health-information reception/analysis side device 2, or the like, and then provides the concealed alteration detection parameter (a hash value or the like) of the distributed analysis result to verify whether alteration has been made.

The decoder 23 includes a medium authentication means 231 that performs mutual authentication between a device and a medium with the device authentication means 2111, a medium file system 232 for accessing the normal region 212, a decoder program 234 for analyzing and controlling browsing/transmitting the health information and the like, and an alteration detection means 233 that detects alteration of the health information passbook/health information 2123, the analysis result information 2124, and the decoder program 234.

The decoder program 234 is for the health-information reception/analysis side device 2 to load the decoder program file 2122 from the normal region 212 and execute it, and includes a browse control means 2341 that controls browsing the health information and analysis result, and transmission to the health-information distribution side device 1, another health-information reception/analysis side device 2, or terminal device 3, and a health information analysis means 2342 that analyzes the health information.

In the present embodiment, it has been described that the transmission/reception unit 22 includes the medium authentication means 221, the medium file system 222, and the alteration detection means 223, and the decoder 23 includes the medium authentication means 231, the medium file system 232, and the alteration detection means 233, but these functions may be shared. However, in either case, the medium authentication means 221 and 231, the medium file systems 222 and 232, and the alteration detection means 223 and 233 are tamper-resistant (obfuscation of software codes), and the software (core software) for these is essential to access the concealed region 211.

In the present embodiment, as described above, it has been described that, as the output of the analysis result by the health-information reception/analysis side device 2, the browse control means 2341 performs display on the health-information reception/analysis side device 2, and that the analysis information container transmission means 2243 performs transmission to the health-information distribution side device 1, the health-information reception/analysis side device 2, or the terminal device 3, but either one of them may be provided as an output means. For example, by allowing only the browse control means 2341 to perform display on the health-information reception/analysis side device 2, the user of the health-information reception/analysis side device 2 may browse the analysis result, or by allowing only the analysis information container transmission means 2243 to perform transmission, the analysis result may be returned to the health-information distribution side device 1, which is the transmission source of the health information and the health information passbook, and reanalysis may be requested to another health-information reception/analysis side device 2 or terminal device 3.

In addition, it has been described that the health-information distribution side device 1 and the health-information reception/analysis side device 2 each have different functions, the present invention is not limited thereto. For example, by connecting a recording medium including information to be stored in the distribution side medium 11 and the reception/analysis side medium 21 to a terminal device having functions of the encoder 12, the distribution unit 13, the transmission/reception unit 22, and the decoder 23, a terminal device that can be used as either of the health-information distribution side device 1 or the health-information reception/analysis side device 2 may be used.

Note that, it is assumed that the programs such as the encoder program file 1121, the distribution program file 1122, the transmission/reception program file 2121, and the decoder program file 2122 are all registered in the management server device 5 beforehand. It is also assumed that attribute information related to each sensor 4 (a sensor identifier for identifying a sensor 4 and other information on the sensor 4) is also stored in the management server device 5 beforehand and can be referred to during analysis.

<Loading of Program, Alteration Detection>

Figure 4:
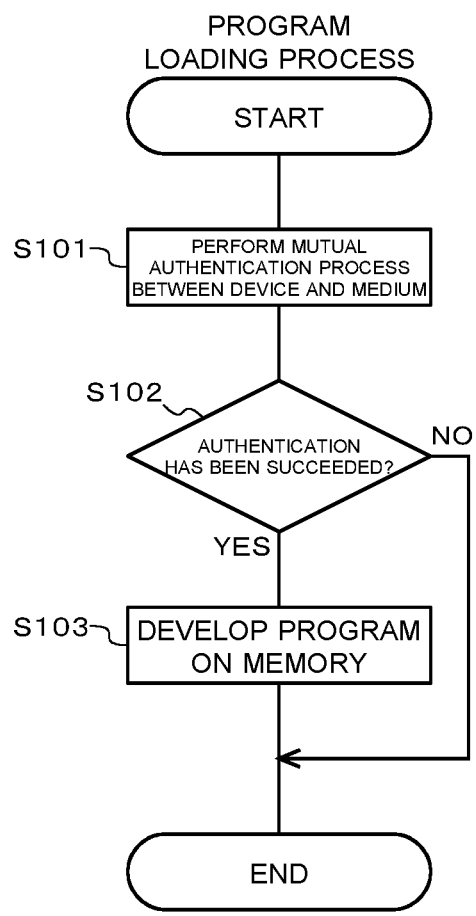
FIG. 4 is a flowchart showing a program loading process in the first embodiment of the present invention.

The encoder program file 1121 and the distribution program file 1122 are loaded when the health-information distribution side device 1 is started. Furthermore, the files may be loaded periodically or when a health information acquisition process is performed based on the user's instruction. FIG. 4 is a flowchart showing the flow of a loading process of the encoder program file 1121.

First, in step S101, the health-information distribution side device 1 and the distribution side medium 11 are mutually authenticated. This process is performed between the medium authentication means 121 and the device authentication means 1111.

Then, when it is determined in step S102 that the authentication process between the device and the medium has been succeeded, the process proceeds to step S103, and the encoder program file 1121 is loaded by the health-information distribution side device 1 as the encoder program 124 and developed on the memory of the health-information distribution side device 1, and the like.

When the authentication has failed in step S102, the encoder program 124 is not loaded in step S103, and the process is terminated. At this time, a message or a log indicating the authentication failure may be output.

A similar process is performed for loading the distribution program file 1122 by the health-information distribution side device 1. Alternatively, the encoder program file 1121 and the distribution program file 1122 are not loaded separately, but may be loaded simultaneously in step S103 after a single authentication process. Furthermore, when the transmission/ reception program file 2121 and the decoder program file 2122 are loaded by the health-information reception/analysis side device 2, a similar process is performed by the health-information reception/analysis side device 2.

Figure 5:
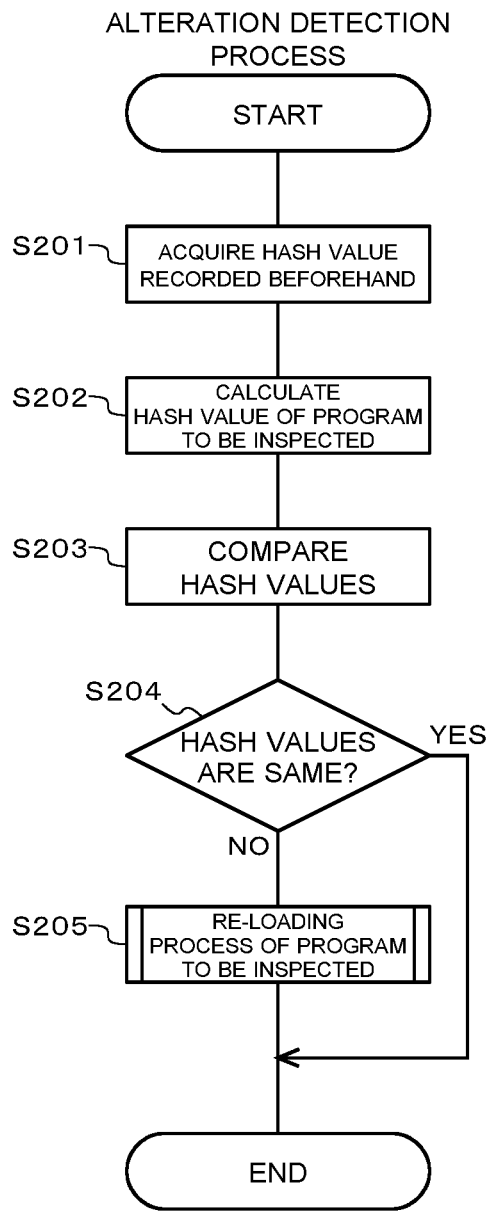
FIG. 5 is a flowchart showing an alteration detection process of a program in the first embodiment of the present invention.

After the program is loaded from the medium authentication means 121 (or the medium authentication means 221) in the above process, the detecting process as to whether the program has been unauthorizedly altered is periodically performed. FIG. 5 is a flowchart showing the flow of an alteration detection process.

First, in step S201, the alteration detection parameter 1114 and the alteration detection parameter 2114 are loaded. In the present embodiment, information including hash values of the encoder program file 1121 and the distribution program file 1122 as the alteration detection parameter 1114 relating to the program, and information including hash values of the transmission/reception program file 2121 and the decoder program file 2122 as the alteration detection parameter 2114 relating to the program is used. Here, the hash value is a value obtained by performing an irreversible calculation process to the original data using a hash function. By calculating and recording a hash value of a normal file beforehand, calculating a hash value of a file the alteration of which is to be detected by a similar procedure in the alteration detection process, and determining whether the hash value is the same as the hash value of the normal file, it is possible to verify whether the file has been altered.

After the hash value recorded as the alteration detection parameters 1114 and 2114 are loaded in step S201, the hash value of the program to be inspected is calculated in step S202. Here, the program to be inspected includes the encoder program file 1121 and the distribution program file 1122 loaded by the health-information distribution side device 1, and the transmission/reception program file 2121 and the decoder program file 2122 loaded by the health-information reception/analysis side device 2.

In the following step S203, the hash values are compared. Here, as described above, when the hash values are the same, it can be determined that the program has not been altered, but when the hash values are different, the program could have been unauthorizedly altered. Thus, when it is determined that the hash values are the same in step S204, the alteration detection process is terminated, but when it is determined that the hash values are not the same in step S204, the process proceeds to step S205, and a re-loading process of the program to be inspected is performed. This is achieved by performing a process described with reference to FIG. 4 again.

On the other hand, when the hash values are not the same and the program could have been altered, it is preferable that the data acquired during the period from the previous alteration detection process to the present time, that is, the data that could have been acquired by the unauthorizedly altered program and has low reliability is discarded or recovered.

Here, when alteration of the encoder program 124 is detected, it is preferable to delete the health information and the health information passbook acquired during the period from the previous alteration detection process to the present time. In addition, since the reliability of the analysis result using the data is low, it is more preferable to request another health-information reception/analysis side device 2, terminal device 3, or the like that hold the analysis result to delete the data.

On the other hand, in the case of detecting alteration of programs other than the encoder program 124, as long as a backup is periodically stored in another health-information distribution side device 1, the health-information reception/analysis side device 2, the terminal device 3, the management server device 5, or other server devices (not shown), there is a possibility that data that is not affected by the alteration of the program, that is, the data having high reliability exists in those server devices or the like. In such a case, it is preferable to acquire such information and to recover the data.

In addition, in the case of detecting alteration of programs other than the encoder program 124, since the data processed by the program the alteration of which is detected, that is, the health information, the health information passbook, and the analysis result transmitted to the health-information reception/analysis side device 2 or the terminal device 3 when alteration of the distribution program 134 is detected, the analysis result and reanalysis result transmitted to the health-information distribution side device 1, another health-information reception/analysis side device 2, terminal device 3, or the like when alteration of the transmission/reception program 224 or the decoder program 234 is detected have low reliability, it is more preferable to request deletion of such data.

In the present embodiment, by verifying whether the program file loaded from the distribution side medium 11 by the health-information distribution side device 1 or the program file loaded from the reception/analysis side medium 21 by the health-information reception/analysis side device 2 has been unauthorizedly altered, and by re-loading the program file when the file could have been altered, it is possible to assure that the health information and the analysis result is not unauthorizedly altered or used.

<Health Information Acquisition Process>

Figure 6:
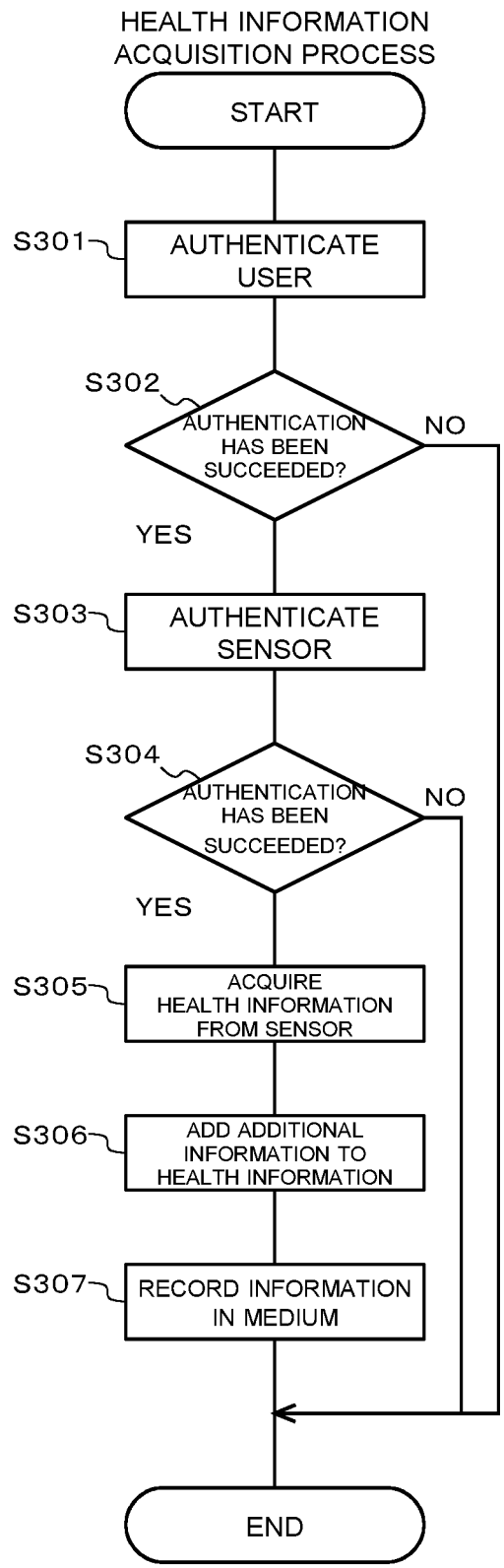
FIG. 6 is a flowchart showing a health information acquisition process in the first embodiment of the present invention.

Next, an acquisition process of the health information from the sensor 4 by the health-information distribution side device 1 will be described. FIG. 6 is a flowchart showing the flow of a health information acquisition process. First, in step S301, the information owner is authenticated by the personal/qualification information authentication means 14. This process is only required to be performed by the authentication means of the health-information distribution side device 1, for example, inputting preset password numbers, and performing biometric authentication such as fingerprint authentication or face authentication, if the health-information distribution side device 1 has such functions of biometric authentication.

When it is determined that the user authentication has been succeeded in step S302, the process proceeds to step S303, and the sensor 4 is authenticated by the sensor authentication means 1241. This is to prevent unauthorized acquisition of the health information generated by people other than the information owner or devices other than the health-information distribution side device 1 and sensors 4 to be targeted, and by listing up identifiers unique to sensors to be targeted by the information owner when the sensor 4 is installed, initially registered, changed in the registration, and by monitoring the content of strange acquisition information, detection and recording in the health information passbook 1123 are performed, and the authentication is performed based on it.

When it is determined that the authentication of the sensor 4 has been succeeded in step S404, the process proceeds to step S305, and the health information storage means 1243 acquires the health information from the sensor 4. In step S306, additional information is added to the health information acquired in step S305. The additional information includes a date/time record (time stamp) when the health information is acquired, and information on the sensor 4 that acquires the information. In this case, it is preferable to add the additional information in a form that is difficult to alter by an electronic certificate issued by a trusted site, an electronic time certificate, or the like.

In step S307, the health information which is acquired in step S305 and to which the additional information is added in step S306 is recorded in the health information passbook 1123 and the health information 1124. The health information is sequentially recorded without overwriting in this step.

With the above process, the health information is acquired using the health-information distribution side device 1. In this manner, by authenticating the information owner and the sensor 4, it is possible to prevent a third person from unauthorizedly recording the health information that is unintended by the information owner. Furthermore, by adding additional information in a form that is difficult to alter to the health information obtained by the sensor 4 and sequentially recording the information without overwriting, it is also possible to prevent the information owner from unauthorizedly altering the health information. For this reason, it is possible to make the health information recorded by the health-information distribution side device 1 highly reliable.

Note that, in FIG. 6, it has been described that the process is immediately terminated when it is determined that the user authentication has failed in step S302 or when the authentication of the sensor 4 has failed in step S304, but an arbitrary process such as a process for requesting re-authentication or for displaying a warning message may be added in such a case.

<Health Information Distribution Process>

Figure 7:
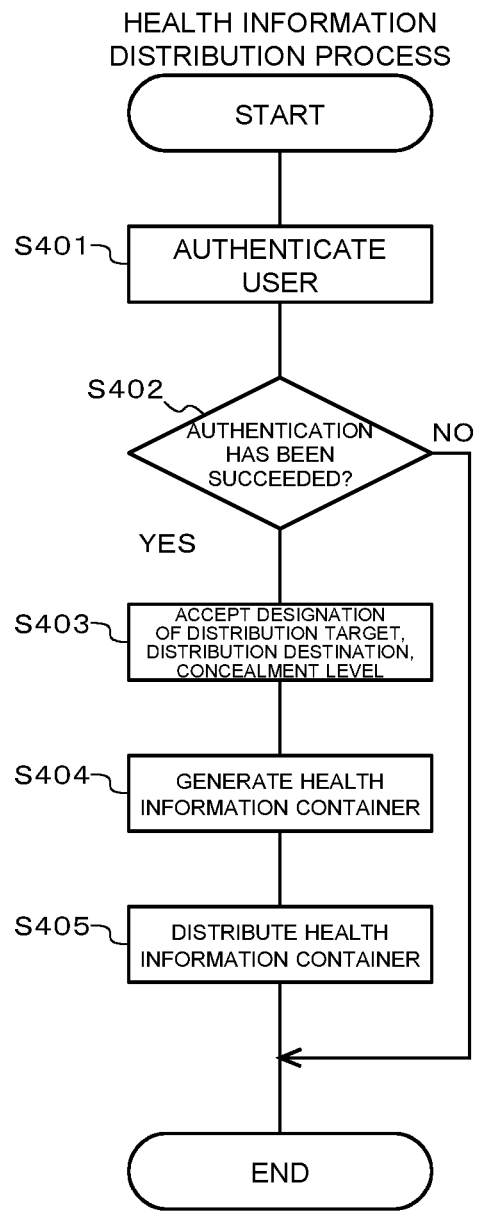
FIG. 7 is a flowchart showing a health information distribution process in the first embodiment of the present invention.

The health information and the health information passbook, which is additional information, acquired with the sensor 4 by the encoder 12 and recorded on the distribution side medium 11 can be distributed to the health-information reception/analysis side device 2 or the terminal device 3. FIG. 7 is a flowchart showing the flow of a health information distribution process.

First, the information owner is authenticated in step S401. This is a similar process to step S301 in the health information acquisition process described with reference to FIG. 6. Then, when it is determined that the user authentication has succeeded in step S403, the distribution process from steps S403 to S405 is performed.

In step S403, designation of information to be distributed among the health information passbook 1123 and health information 1124, and designation of the distribution destination and a concealment level to be used for distribution are accepted from the information owner. The designation of the information to be distributed in this step is only required to be accepted by any method, for example, information acquired from a specific sensor 4, information acquired in a specific period, or the like. The designation of the distribution destination is also only required to be accepted by any method, such as a method of designating the health-information reception/analysis side device 2 or the terminal device 3 directly connected wiredly or wirelessly, or a method of designating a uniform resource locator (URL) in the case of connection via the network NW. Alternatively, the health-information reception/analysis side device 2 or the terminal device 3 connected by a predetermined method such as wired connection may be automatically selected as the distribution destination. As the concealment level, a selection of any one of the four classes 0 to 3 as shown in Table 1 is accepted. Alternatively, the concealment level used for distribution may be determined beforehand for the information to be distributed, and the health-information reception/analysis side device 2 or the terminal device 3 which is the distribution destination.

In the following step S404, based on the designation received from the information owner in step S403, a generation process of a health information container is performed. The health information container in this description is a container for distributing information to be distributed among the health information and the health information passbook with the concealment level designated from the information owner. The container may be a single file or a collection of multiple files.

Note that, when the health information container or the analysis information container is transmitted to the terminal device 3 that does not have a secure recording medium like the reception/analysis side medium 21, a process for setting the concealment level to class 0, or for omitting setting of the concealment level itself at the time of generating a health information container is performed.

Then, in step S405, the health information container is transmitted to the distribution destination, and the health information distribution process is terminated. In addition to the user authentication in step S401 and accepting of various designations from the information owner in step S403 as described above, the health information distribution process may be performed periodically automatically without the user authentication in step S401 by periodically setting distribution of the health information beforehand.

Furthermore, according to the distribution of the health information container in step S405, the alteration detection parameter concealing distribution means 136 may also distribute the alteration detection parameter of the health information or the health information passbook included in the health information container.

<Health Information Reception/Analysis Process>

Figure 8:
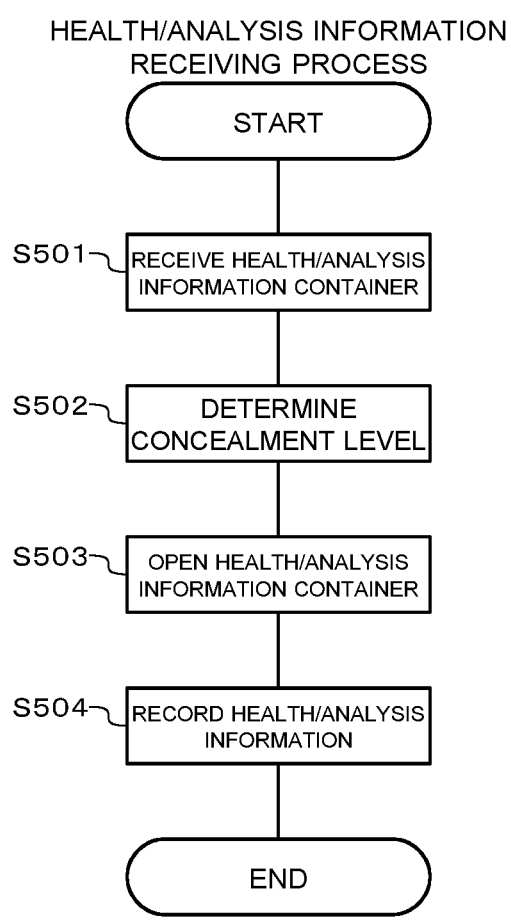
FIG. 8 is a flowchart showing a health/analysis information receiving process in the first embodiment of the present invention.

Next, a reception process of the health information container distributed from the health-information distribution side device 1 by the health-information reception/analysis side device 2 will be described. Note that, a similar process is also performed when the analysis information container which is the analysis result of the health information container is received from another health-information reception/analysis side device 2 or terminal device 3, and this process will be described together. FIG. 8 is a flowchart showing the flow of the reception process of the health information container and the analysis information container by the health-information reception/analysis side device 2.

After the health information container or the analysis information container is received in step S501, the concealment level is determined in step S502. This is executed by attaching, to the health information container or the analysis information container, information indicating the concealment level which can be determined without opening the container, and reading it.

Then, according to the concealment level determined in step S502, the health information container or the analysis information container is opened in step S503. This process is different depending on the concealment level. For example, it is only necessary to expand the container in the case of data set to class 0, but a decryption process of encrypted data is included in the case where the concealment level is set to class 1 or higher. Furthermore, in the case of data set to class 2 or higher, a process for acquiring additional information such as copying restriction and validity period set to the data is also included.

In step S504, the health information or the health information passbook obtained by opening the health information container, or the analysis result information obtained by opening the analysis information container is recorded in the health information passbook/health information 2123, and the reception process is terminated.

The reception process as described above may be performed at an arbitrary timing. For example, the process is performed periodically, performed when an instruction from a user using the health-information reception/analysis side device 2 or the terminal device 3 is received, or performed every time the health-information distribution side device 1 distributes the health information, or another health-information reception/analysis side device 2 or terminal device 3 distributes the analysis information container.

In addition, as described above, when the health-information distribution side device 1 transmits the alteration detection parameter from the alteration detection parameter concealing distribution means 136 according to the distribution of the health information container, the alteration detection parameter may be received by the health-information reception/analysis side device 2 and whether the data has been altered may be verified after the opening process in step S503.

<Health Information Analysis/Analysis Information Reanalysis Process>

FIG. 9 is a flowchart showing a process for analyzing the health information received from the health-information distribution side device 1 and a process for reanalyzing the analysis information received from another health-information reception/analysis side device 2 or terminal device 3 in the health-information reception/analysis side device 2. First, in step S601, the health information or the health information passbook is read from the health information passbook/health information 2123.

Then, the health information is analyzed and the analysis information is reanalyzed by the health information analysis means 2342 in step S602, and the result is temporarily recorded in the analysis result information 2124 in step S603. In this step, information on the sensor 4 with which the health information has been acquired from the management server device 5 is acquired using the sensor identifier included in the health passbook information read in step S601, and analysis based on the acquired information or the like is performed. With this analysis, by, for example, analyzing, by AI or the like, behavior information such as activity amount and position information during the day, environmental information such as pollen/air pollution, atmospheric pressure, and temperature during movement, and biological information such as stress and blood-pressure change, which are transmitted by the health information container, and by visualizing the mutual relations, it is possible to obtain a result that can be used for presymptomatic-disease measures, medical treatment, and product development based on big data, or the like.

Note that, the analysis result may be held not temporarily but retained (within a range permitted by the concealment level set to the health information), or only history information indicating that the analysis has been performed may be retained. With this configuration, it is possible for the information owner who is the distribution source of the health information to easily perform verification.

Thereafter, in step S604, the analysis information container transmission means 2243 transmits the analysis result temporarily recorded in the analysis result information 2124. The transmission destination in this step may be, in the case of the analysis result of the health information received from the health-information distribution side device 1, the health-information distribution side device 1 which is the distribution source, or may be, in the case of further analyzing or storing the analysis result with/in another health-information reception/analysis side device 2 or terminal device 3, the device after the concealment level is set. Alternatively, designation of an arbitrary transmission destination may be accepted from the user.

Note that, when the health information container or the analysis information container is transmitted to the terminal device 3 that does not have a secure recording medium like the reception/analysis side medium 21, a process for transmitting the container after setting the concealment level to class 0, or of omitting setting of the concealment level itself is performed.

Here, according to the transmission of the analysis information container in step S604, the alteration detection parameter concealing distribution means 226 may transmit the alteration detection parameter of the analysis result.

It has been described that the process for transmitting the analysis result of the health information to the health-information distribution side device 1, another health-information reception/analysis side device 2, or terminal device 3, but the user using the health-information reception/analysis side device 2 can also browse the analysis result with the browse control means 2341. Here, both processes of the transmission to another device by the analysis information container transmission means 2243 and the browsing by the user with the browse control means 2341 are performed according to the concealment level designated in the original health information container (or analysis information container). In other words, when the concealment level of the original health information container or analysis information container is set to class 2 or higher and when data copy restriction and validity period are set, browsing restriction, deletion of expired data, or the like is performed according to the setting.

<File Recording/Reading Process by Medium File System>

In step S307 in the process for acquiring health information, step S404 in the process for distributing the health information, step S504 in the process for receiving the health information or the analysis information, and steps S601 and S603 in the process for analyzing the health information and for reanalyzing the analysis information, when data is read or written from/to the normal region 112 of the distribution side medium 11 or the normal region 212 of the reception/analysis side medium 21, a process for making the data difficult to alter with the medium file system 122, 132, 222, and 232 is performed.

FIG. 10A is a flowchart showing the flow of a data recording process by the medium file systems 122, 132, 222, and 232. To record data, first, a hash value of the data to be recorded is calculated in step S701. That is the data alteration detection parameter used to detect alteration of data.

In step S702, the data to be recorded is encrypted using the data encryption key 1113 and 2113. In step S703, the hash value calculated in step S701 is recorded in the concealed regions 111 and 211, and the data encrypted in step S702 is recorded in the normal regions 112 and 212. Note that, the recording of data in step S702 is performed sequentially without overwriting.

The data recorded in the normal regions 112 and 212 in this manner is read in a flow as shown in FIG. 10B. First, in step S801, the encrypted data is decrypted. For this decryption, the data encryption keys 1113 and 2113 are used.

Then, a hash value of the decrypted data is calculated in step S802, and the calculated hash value is compared with the hash value recorded in the concealed regions 111 and 211 in step S803. Here, when the hash values do not match, there is a high possibility that data has been altered. Thus, when it is determined that the hash values do not much in step S804, the process proceeds to step S805 to delete or recover the data.

The recovery of data in this step is achieved by, for example, a method of storing a backup in the management server device 5 or another server device (not shown) beforehand at the time of recording the data or by a periodic process, and acquiring it.

In addition, when alteration of the data is detected, it is preferable to perform the alteration detection process to the data existing on other terminals and the analysis result.

As described above, by reading and writing data in combination with the encryption and the alteration detection using hash values, it is possible to store data safely and prevent unauthorized alteration. Furthermore, it is preferable to perform an alteration detection process of data as shown in FIG. 10B by a process based on a user's instruction, a periodic process, or the like.

In the present embodiment, it has been described that the program executed by the health-information distribution side device 1 or the health-information reception/analysis side device 2, the health information, the health information passbook, the analysis information, and the like are stored in the distribution side medium 11 or the reception/analysis side medium 21, but the present invention is not limited to this. For example, as long as a link such as a URL or a path for accessing information is securely stored in the distribution side medium 11 or the reception/analysis side medium 21, and the information as described above can be eventually accessed using the link, the programs and information are not necessarily stored in the distribution side medium 11 or the reception/analysis side medium 21. With this configuration, when the storage capacity of the distribution side medium 11 is limited, it is possible to store a lot of information in a server device communicable via the network NW and storage units provided in the health-information distribution side device 1 and the health-information reception/analysis side device 2.

As described above, the information owner determines the handling of information by setting the concealment level, and alteration of the programs used for the health information and the analysis information, and of the health information and the analysis information itself are prevented, whereby it is possible for the information owner to grasp the own information, determine the utilization policy and the distribution destination of the information to be used, set the validity period, and erase the distributed information.

As a result, it is possible to solve the problems that information is collected without noticing it and it is difficult for the information owner who generated the information to grasp the whereabouts of the processed information once collected in a cloud like traditional cloud-based data utilization, and that a business operator who uses the information is entrusted with the protection from information alteration and alteration can be unauthorizedly made. Furthermore, by providing information utilization with a configuration based on the P2P communication using a device such as a smartphone and a medium such as a secure SD card, which are widely spread, without depending on a specific cloud server, it is possible to achieve easily flexibly acquisition, storage, distribution, and process of highly reliable health information without major investment and infrastructure remodeling.

Second Embodiment

Hereinafter, a second embodiment of the present invention will be described in detail with reference to the drawings. Note that, the same reference signs are attached to the basically same component elements as those in the above first embodiment, and the description thereof is simplified. As described in the first embodiment with reference to FIG. 1, a system using an information management terminal device according to the present embodiment includes a health-information distribution side device 1, a health-information reception/analysis side device 2, a terminal device 3, a sensor 4, and a management server device 5. However, the present embodiment is different in that a more general recording medium is used as a distribution side medium 11 and a reception/analysis side medium 21 instead of a recording medium the security of which is enhanced as described in the first embodiment, and that the management server device 5 not only stores information on the sensor 4 but also includes information included in a concealed region 111.

<Configuration of Health-Information Distribution Side Device>

Figure 11:
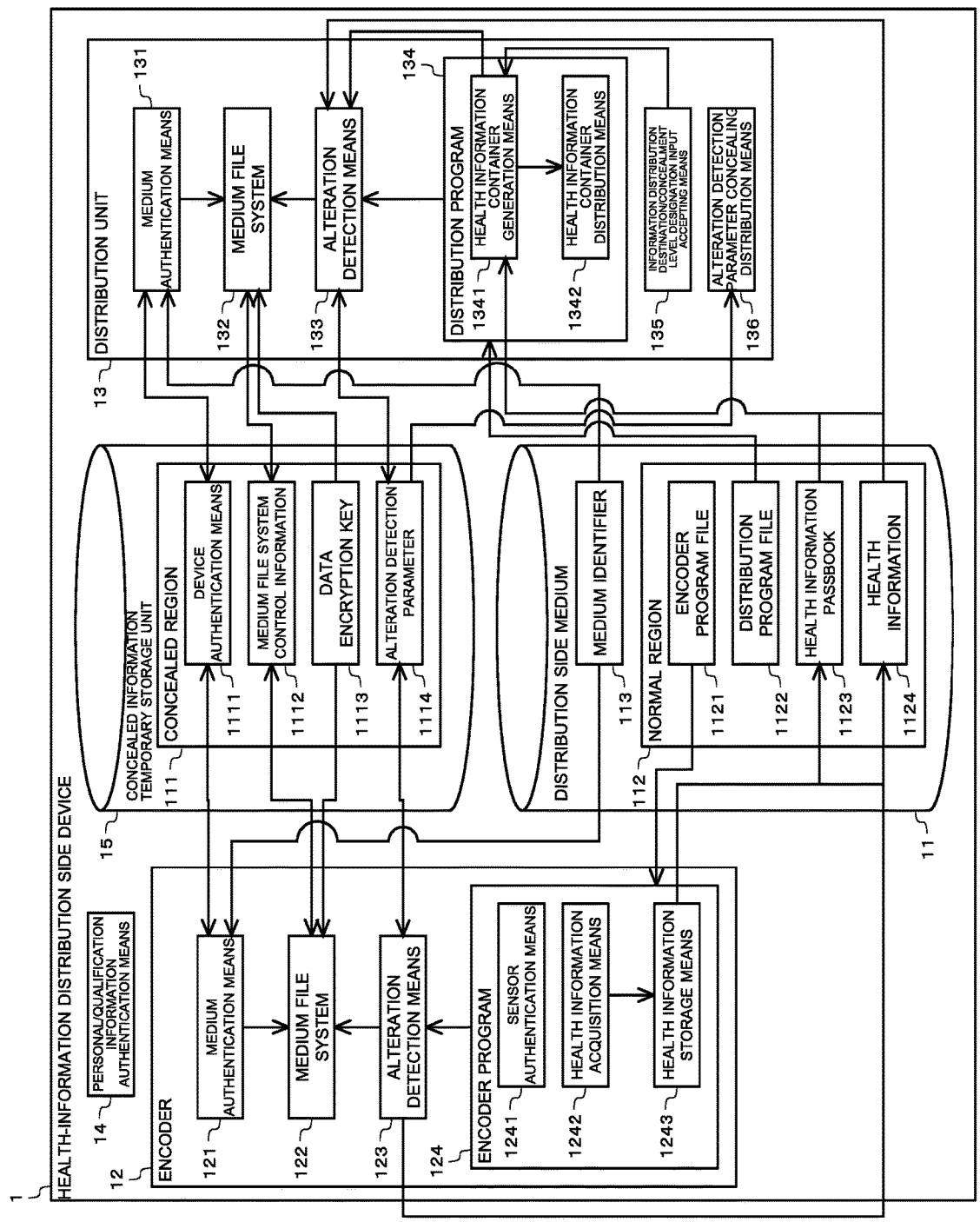
FIG. 11 is a functional block diagram of a health-information distribution side device according to a second embodiment of the present invention.

FIG. 11 shows a functional block diagram of the health-information distribution side device 1 according to the present embodiment. As shown in this drawing, the health-information distribution side device 1 according to the present embodiment includes an encoder 12, a distribution unit 13, and a personal/qualification information authentication means 14 similar to the first embodiment. The second embodiment differs from the first embodiment in that the distribution side medium 11 includes a normal region 112, and a medium identifier 113, and that a concealed information temporary storage unit 15 is provided. In other words, in the present embodiment, a recording medium including the concealed region 111 and the normal region 112 such as the SeeQVault exemplified in the first embodiment is not used, but a more general recording medium that has the normal region 112 (and the medium identifier 113) but does not have the concealed region 111 is used.

As to be described later, the concealed information temporary storage unit 15 is a region for storing information received from the management server device 5 and to be included in the concealed region 111, and is secured on a volatile or nonvolatile memory of the health-information distribution side device 1 beforehand, or when information to be included in the concealed region 111 is received from the management server device 5.

Alternatively, a region used as the concealed information temporary storage unit 15 may be secured in the normal region 112 of the distribution side medium 11.

The medium identifier 113 is an identifier unique to each distribution side medium 11 and cannot be rewritten by the user. For example, since an SD card has a region called a card identification (CID) which includes a serial number and the like and which cannot be rewritten by the user, when an SD card is used as the distribution side medium 11, the CID can be used as the medium identifier 113.

Also in the present embodiment, information included in the normal region 112 may be held as a link instead of the entity thereof in a server device communicable via a network NW, or the storage unit of the health-information distribution side device 1.

<Configuration of Health-Information Reception/Analysis Side Device>

Figure 12:
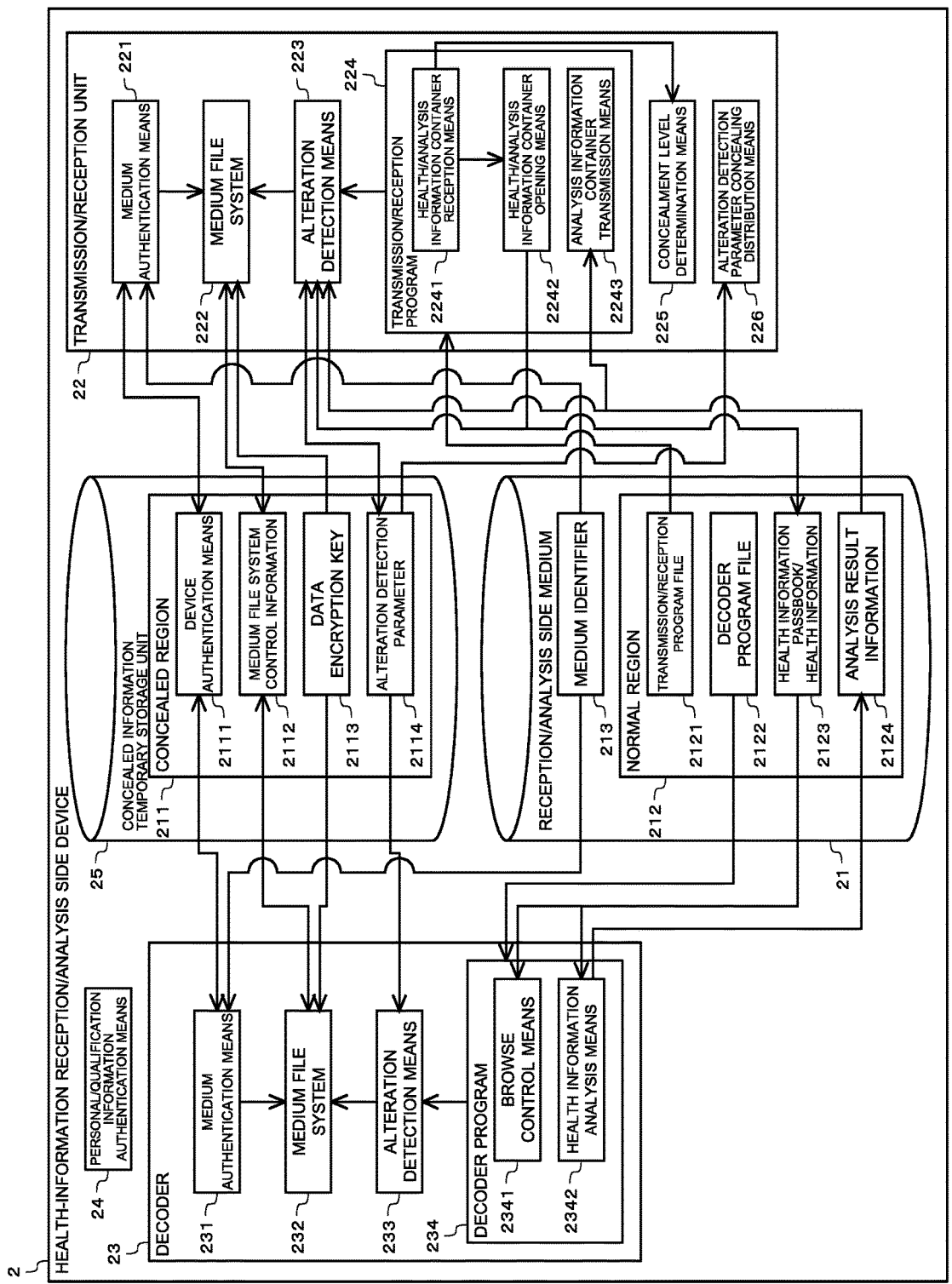
FIG. 12 is a functional block diagram of a health-information reception/analysis side device according to the second embodiment of the present invention.

FIG. 12 shows a functional block diagram of the health-information reception/analysis side device 2 according to the present embodiment. As shown in this drawing, the health-information reception/analysis side device 2 according to the present embodiment includes a transmission/reception unit 22, a decoder 23, and a personal/qualification information authentication means 24 similar to the first embodiment. The second embodiment differs from the first embodiment in that the reception/analysis side medium 21 includes a normal region 212 and a medium identifier 213, and that a concealed information temporary storage unit 25 is provided. In other words, similarly to the health-information distribution side device 1 according to the present embodiment, a recording medium including the concealed region 211 and the normal region 212 such as the SeeQVault exemplified in the first embodiment is not used, but a more general recording medium that has the normal region 212 (and the medium identifier 213) but does not have the concealed region 211 is used.

Similarly to the concealed information temporary storage unit 15, the concealed information temporary storage unit 25 is secured on the health-information reception/analysis side device 2 or the normal region 212 of the reception/analysis side medium 21 beforehand, or when the concealed region 211 is received from the management server device 5.

Similarly to the medium identifier 113, as the medium identifier 213, an identifier unique to a recording medium used as the reception/analysis side medium 21, that is, the value included in the CID register is used when an SD card is used as the reception/analysis side medium 21.

Also in the present embodiment, information included in the normal region 212 may be held as a link instead of the entity thereof in a server device communicable via a network NW, or the storage unit of the health-information reception/analysis side device 2. With this configuration, when the storage capacity of the reception/analysis side medium 21 is limited, it is possible to store a lot of information.

<Reception of Concealed Information, Loading of Program, Alteration Detection>

Figure 13:
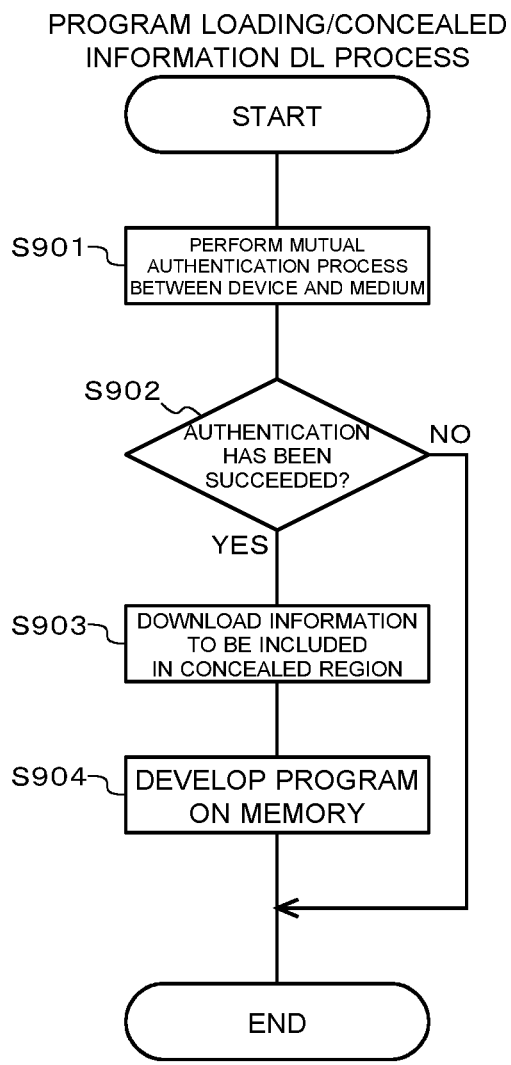
FIG. 13 is a flowchart showing a program loading process in the second embodiment of the present invention.

In the present embodiment, when the health-information distribution side device 1 is started or when an encoder program file 1121 or a distribution program file 1122 is loaded by a periodic process or a process according to the user's instruction, the concealed region 111 is received from the management server device 5. FIG. 13 is a flowchart showing the flow of the reception of the concealed region 111 and a loading process of the encoder program file 1121 or the distribution program file 1122. It can be also described that this process corresponds to the process described with reference to FIG. 4 in the first embodiment.

First, in step S901, an authentication process between the health-information distribution side device 1 and the management server device 5 is performed. This is performed by acquiring the medium identifier 113 from the distribution side medium 11 by a medium authentication means 121 or 221 and transmitting it to the management server device 5.

Then, when it is determined that the authentication process has succeeded in step S902, the process proceeds to step S903, and the information to be included in the concealed region 111 is downloaded from the management server device 5. This is performed in a procedure in which the medium identifier 113 and the information corresponding to the medium identifier 113 and to be included in the concealed region 111 are associated and stored in the management server device 5 beforehand, and the information corresponding to the medium identifier 113, to be included in the concealed region 111, and received by the management server device 5 in step S901 is transmitted from the management server device 5 to the health-information distribution side device 1 in step S903.

In step S903, the concealed region 111 is recorded in the concealed information temporary storage unit 15. Here, if the region to be used as the concealed information temporary storage unit 15 is not secured beforehand, the securing process is performed first. Here, similarly to the case where the concealed region 111 is included in the distribution side medium 11 in the first embodiment, the concealed region 111 can be accessed only when the mutual authentication between the device and the medium, that is, between the device authentication means 1111 and the medium authentication means 121 or 131 is established.

Thereafter, in step S904, similarly to the process performed in step S103 in FIG. 4 in the first embodiment, loading of the encoder program file 1121 as an encoder program 124 and loading of the distribution program file 1122 as a decoder program 234 are performed.

In this manner, the concealed region 111, the encoder program 124, and the distribution program 134 on the health-information distribution side device 1 are prepared. Furthermore, when the concealed region 211, a transmission/reception program file 2121, and a decoder program file 2122 are loaded on the health-information reception/analysis side device 2, a similar process is performed by the health-information reception/analysis side device 2.

As described above, by performing the authentication process using the medium identifier 113 or 213 and downloading the information to be included in the concealed region 111 and the concealed region 211 from the management server device 5, it is possible to implement the health-information distribution side device 1 and the health-information reception/analysis side device 2 according to the present invention using a normal SD card or the like instead of a special recording medium having a concealed region and a normal region.

In the present embodiment, it has been described that the medium identifier 113 or the medium identifier 213 is transmitted to the management server device 5 to perform the authentication process between the device and the server in the step S901. However, by further transmitting an identifier unique to the health-information distribution side device 1 or the health-information reception/analysis side device 2 (for example, the MAC address of the communication unit of the device, the serial number of the device, or the like) at the same time, and storing the correspondence relation between the device and the recording medium in the management server device 5, the information may be verified in the authentication process. With this configuration, it is possible to implement the health-information distribution side device 1 and the health-information reception/analysis side device 2 according to the present embodiment only when the device and the recording medium which are registered beforehand, and to make unauthorized acts such as alteration more difficult.

With the above process, after the concealed regions 111 and 211 are downloaded and recorded in the health-information distribution side device 1 and the health-information reception/analysis side device 2, and the programs are loaded in the devices, as described in the first embodiment, the alteration process of the program shown in FIG. 5, the acquisition process of the health information from the sensor 4 by the health-information distribution side device 1 as shown in FIG. 6, the distribution process of the health information to the health-information reception/analysis side device 2 or the terminal device 3 by the health-information distribution side device 1 as shown in FIG. 7, the analysis process of the health information by the health-information reception/analysis side device 2 as shown in FIG. 8, and the like are performed.

The writing and reading process of the health information or the health information passbook by the health-information distribution side device 1 and the health-information reception/analysis side device 2 is performed similarly to the process in the first embodiment as shown in FIG. 10. However, after the information in the concealed region 111 or 211 is updated such as updating of the medium file system control information 1112 or 2112 according to the writing of the data, or writing of the hash value for the alteration detection to the concealed region 111 or 211, uploading to the management server device 5 is sequentially or periodically performed, and the information associated with the medium identifier 113 or 213, recorded in the management server device 5, and to be included in the concealed region 111 or 211 is updated.

In the present specification, it has been described that the health-information distribution side device 1 and the health-information reception/analysis side device 2 are implemented using a secure recording medium in the first embodiment, and that the health-information distribution side device 1 and the health-information reception/analysis side device 2 are implemented using a more general recording medium in the second embodiment. However, the health information and the analysis information may be mutually exchanged between the health-information distribution side device 1 and the health-information reception/analysis side device 2 described in each embodiment, that is, between the health-information distribution side device 1 described in the first embodiment and the health-information reception/analysis side device 2 described in the second embodiment, between the health-information distribution side device 1 described in the second embodiment and the health-information reception/analysis side device 2 described in the first embodiment, or between the health-information reception/analysis side device 2 described in the first embodiment and the health-information reception/analysis side device 2 described in the second embodiment.

Third Embodiment

Hereinafter, a third embodiment of the present invention will be described in detail with reference to the drawings. Note that, the same reference signs are attached to the basically same component elements as those in the above first embodiment, and the description thereof is simplified. As described in the first embodiment with reference to FIG. 1, a system using an information management terminal device according to the present embodiment includes a health-information distribution side device 1, a health-information reception/analysis side device 2, a terminal device 3, a sensor 4, and a management server device 5. As described in the first embodiment, the acquisition process of the health information from the sensor 4 by the health-information distribution side device 1 as shown in FIG. 6, the distribution process of the health information to the health-information reception/analysis side device 2 or the terminal device 3 by the health-information distribution side device 1 as shown in FIG. 7, the analysis process of the health information by the health-information reception/analysis side device 2 as shown in FIG. 8, and the like are performed.

However, in the system using the information management terminal device according to the present embodiment, the process related to the recording and reading of data and the process related to the alteration detection of the program are different from those described in the first embodiment.
<Configuration of Health-Information Distribution Side Device>

Figure 14:
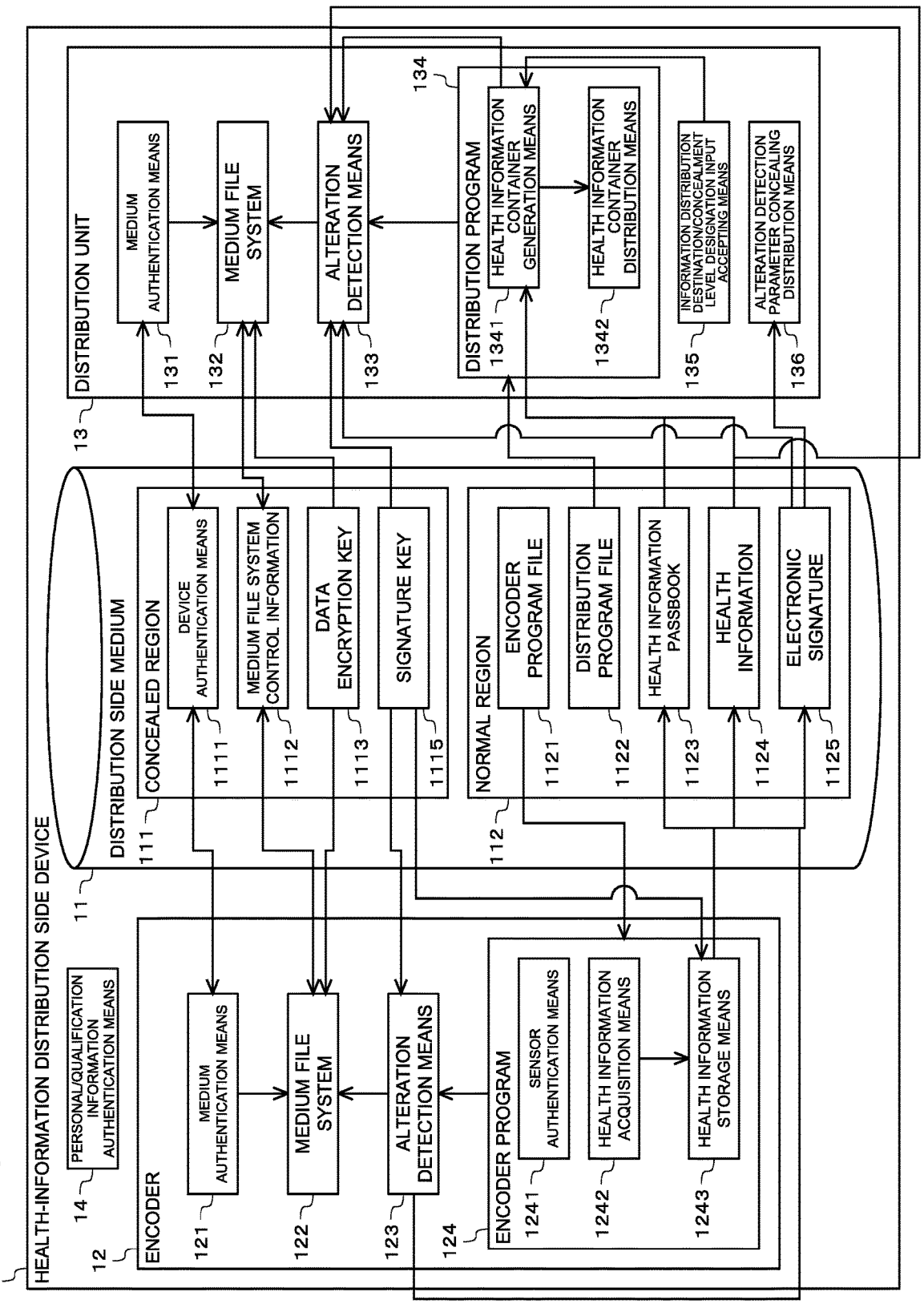
FIG. 14 is a functional block diagram of a health-information distribution side device according to a third embodiment of the present invention.

FIG. 14 shows a functional block diagram of the health-information distribution side device 1 according to the present embodiment. As shown in this drawing, similarly to the first embodiment, the health-information distribution side device 1 according to the present embodiment includes a distribution side medium 11 which is a recording medium having a concealed region 111 and a normal region 112 such as the SeeQVault, an encoder 12, a distribution unit 13, and a personal/qualification information authentication means 14.

In the first embodiment, the hash value of data or a program to be inspected is stored in the concealed region 111 as the alteration detection parameter. In contrast, in the present embodiment, the concealed region 111 has a signature key 1115 as an alteration detection parameter, and the normal region 112 has an electronic signature 1125 for a health information passbook 1123 and health information 1124.

In the present embodiment, the hash value itself of data or a program to be subjected to the alteration detection is stored in the normal region 112. The hash value is encrypted, and the signature key 1115 for generating an electronic signature is held in the concealed region 111 as the alteration detection parameter. In the present embodiment, a case in which a pair of a secret key and a public key is held as the signature key 1115 to use the public key encryption technique and the public key among them is used as the signature key will be exemplified. Alternatively, only the secret key may be held as the signature key 1115, and the public key paired therewith may be acquired from an external server or the like (not shown) as necessary.

Regarding the data encryption, a common key may be held as a data encryption key 1113 to use a common key encryption method, or a pair of a secret key and a public key is held as the data encryption key 1113 to use a public key encryption method. Alternatively, only the secret key may be held as the data encryption key 1113, and the public key paired therewith may be acquired from an external server or the like (not shown) as necessary.

Also in the present embodiment, information included in the normal region 112 may be held as a link instead of the entity thereof in a server device communicable via a network NW, or the storage unit of the health-information distribution side device 1.
<Configuration of Health-Information Reception/Analysis Side Device>

Figure 15:
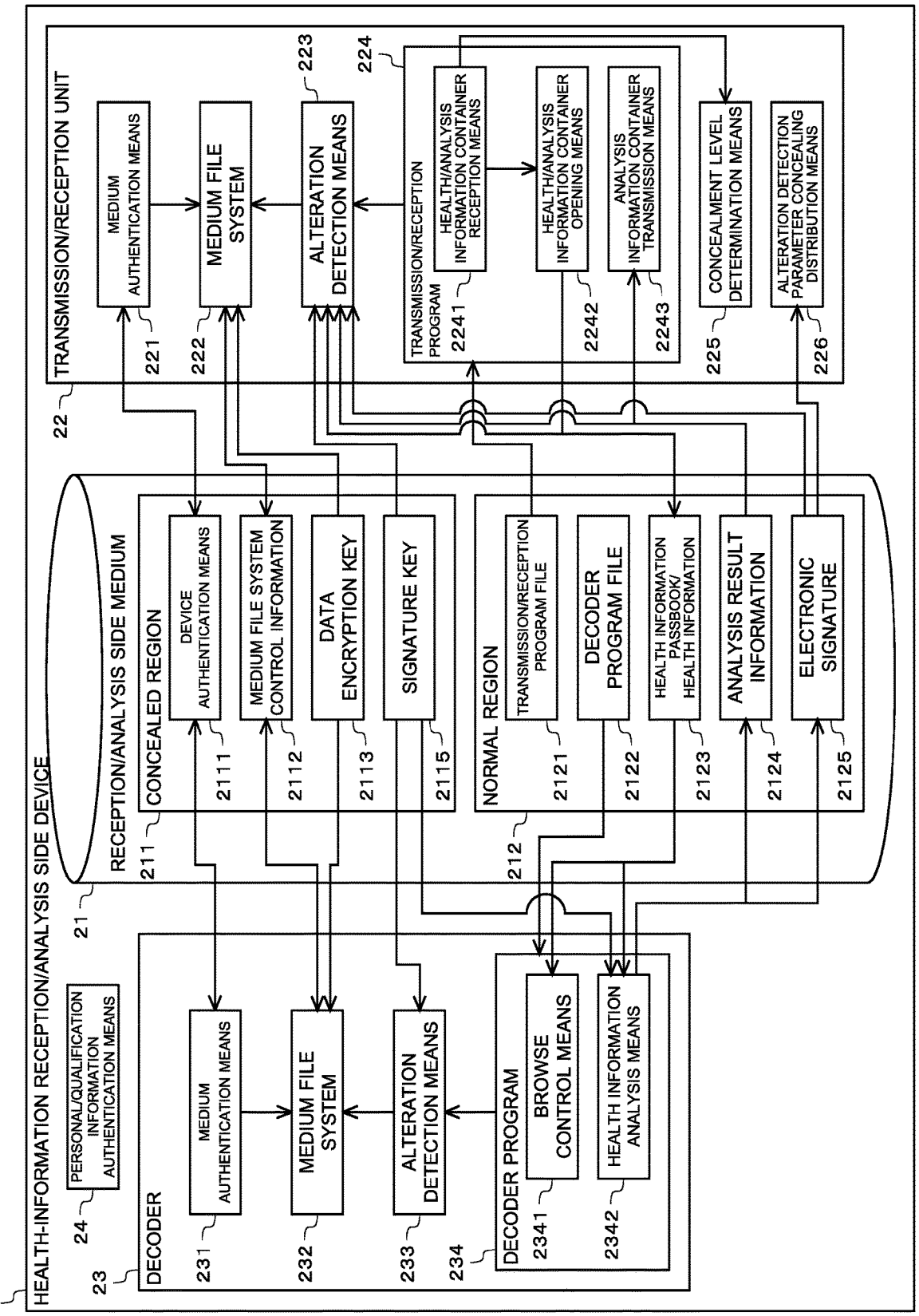
FIG. 15 is a functional block diagram of a health-information reception/analysis side device according to the third embodiment of the present invention.

FIG. 15 shows a functional block diagram of the health-information reception/analysis side device 2 according to the present embodiment. As shown in this drawing, similarly to the first embodiment, the health-information reception/analysis side device 2 according to the present embodiment includes a reception/analysis side medium 21 which is a recording medium having a concealed region 211 and a normal region 212 such as the SeeQVault, a transmission/reception unit 22, a decoder 23, and a personal/qualification information authentication means 24.

Then, similarly to the health-information distribution side device 1 according to the present embodiment described above with reference to FIG. 14, the concealed region 211 includes a signature key 2115 as the alteration detection parameter, and the normal region 112 includes an electronic signature 2125 for health information passbook/health information 2123 and analysis result information 2124.

Regarding the signature key 2115 here, similarly to the signature key 1115 in the health-information distribution side device 1 described above, a case in which a pair of a secret key and a public key is held as the signature key 2115, and the public key among them is used as the signature key will be exemplified. Alternatively, only the secret key may be held as the signature key 2115, and the public key paired therewith may be acquired from an external server or the like (not shown) as necessary.

Regarding a data encryption key 2113 here, similarly to the data encryption key 1113 in the health-information distribution side device 1 described above, a common key may be used as the data encryption key 2113 to use a common key encryption method to encrypt data, or a pair of a secret key and a public key used to encrypt data or only a secret key may be held as data encryption key 2113 to use a public key encryption method to encrypt data.

Also in the present embodiment, information included in the normal region 212 may be held as a link instead of the entity thereof in a server device communicable via a network NW, or the storage unit of the health-information reception/analysis side device 2. With this configuration, when the storage capacity of the reception/analysis side medium 21 is limited, it is possible to store a lot of information.

<File Recording/Reading Process by Medium File System>

In the health-information distribution side device 1 and the health-information reception/analysis side device 2 according to the present embodiment, data is read and written using the signature key 1115 or 2115 as the alteration detection parameter. FIG. 16A is a flowchart showing a data recording process in the present embodiment.

First, in step S1001, data is encrypted with the data encryption key 1113. The encrypted data obtained thereby is recorded in the normal region 112 or 212 in step S1002.

Then, in step S1003, a hash value of the encrypted data is calculated. In this step, a process using a predetermined arbitrary hash function is performed. The hash value of the data calculated in step S1003 is encrypted with the public key of the signature key 1115 or the signature key 2115 in step S1004. This process is to add an electronic signature using the signature keys 1115 or 2115 to the encrypted data.

Finally, in step S1005, the electronic signature is recorded in the normal region 112 or 212, and the data recording process is terminated.

In this manner, by holding the signature key, instead of the hash value itself, for encrypting the hash value and generating the electronic signature as the alteration detection parameter in the concealed region 111 or 211, it is possible to store data in a form to which the alteration detection process can be performed later when data capacity of the concealed region 111 or 211 is limited.

Next, with reference to FIG. 16B, a data reading process in the present embodiment will be described. First, in step S1101, a hash value of the encrypted data to be read is calculated.

Then, in step S1102, the electronic signature attached to the encrypted data is decrypted. As described above, in the present embodiment, a case in which the public key encryption technique is used and the public key among the pair of the secret key and the public key is used as the signature key is exemplified. For this reason, for decrypting the electronic signature in this step, the secret key paired with the public key used for generating the electronic signature in step S1004 in the data recording process is used.

In step S1103, the hash value calculated from the encrypted data in step S1101 and the hash value obtained by decrypting the electronic signature in step S1102 are compared. Here, when it is determined that these hash values are the same, it is determined that the data has not been altered, and the process proceeds from step S1104 to step S1105 to decrypt the data.

Here, when the common key method is used to encrypt data, decryption is performed with the same key as the key used to encrypt the data. Alternatively, when the public key method is used to encrypt data, decryption is performed with the secret key (or public key) paired with the public key (or secret key) used to encrypt the data.

On the other hand, when it is determined that the hash values do not match as a result of comparison of the hash values in step S1103, the data could have been altered. Thus, the process proceeds from step S1104 to step S1106, and a process for deleting or recovering the data is performed. The recovery of the data in this step is performed by an arbitrary method, for example, by storing a backup of the data in a predetermined server beforehand and acquiring it. Alternatively, a process for trying to recover data first and the data may be deleted only when the recovery has failed.

By recording and reading the data in the above manner, it is possible to use the signature key 1115 or 2115 as the alteration detection parameter and to handle the data in a state where alteration can be detected.

<Alteration Detection Process of Program>

Figure 17:
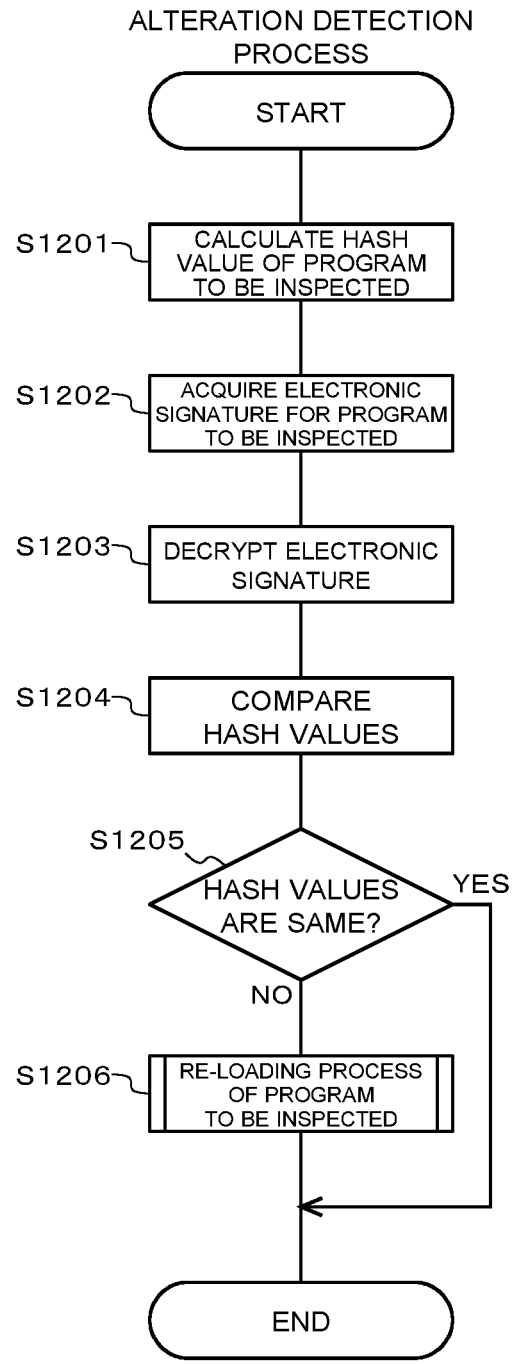
FIG. 17 is a flowchart showing an alteration detection process of a program in the third embodiment of the present invention.

Next, with reference to the flowchart shown in FIG. 17, an alteration detection process of a program in the present embodiment will be described. This shows the flow of the alteration detection process of the encoder program file 1121 or the distribution program file 1122 in the health-information distribution side device 1, or the transmission/reception program file 2121 or the decoder program file 2122 in the health-information reception/analysis side device 2.

First, in step S1201, a hash value of the program to be inspected is calculated. Then, in step S1202, the electronic signature for the program to be inspected is acquired. Here, the electronic signature may be recorded in the normal region 112 or 212 together with the program beforehand, or may be received as appropriate from an external server or the like when the alteration detection process of the program is performed. The electronic signature acquired in this step is the hash value calculated from a legitimate program and encrypted with the public key of the signature key 1115 or the signature key 1115.

Then, in step S1203, the electronic signature is decrypted. For the decryption in this step, the secret key of the signature key 1115 or the signature key 1115 is used.

In this manner, the hash value of the program to be inspected is obtained.

In step S1204, the hash value calculated from the program to be inspected in step S1201 and the hash value obtained by decrypting the electronic signature in step S1203 are compared. Here, when it is determined that these hash values are the same, it is determined that the program has not been altered, and the process is terminated at step S1205.

On the other hand, when it is determined that the hash values do not match as a result of comparison of the hash values in step S1204, the program could have been altered. Thus, the process proceeds from step S1205 to step S1206 to reload the inspected program. Note that, the reloading process of the program in step S1206 may be performed by a similar process to the process described with reference to FIG. 4 in the first embodiment.

<Data Exchange Between Devices>

It is preferable that the data encryption keys 1113 and 2113 and the signature keys 1115 and 2115 in the information management terminal device according to the present embodiment are different from each device. In this configuration, it is possible to exchange more secure information between devices by exchanging the data encryption key and the signature key using the alteration detection parameter concealing distribution means 136 or 226.

Figure 18:
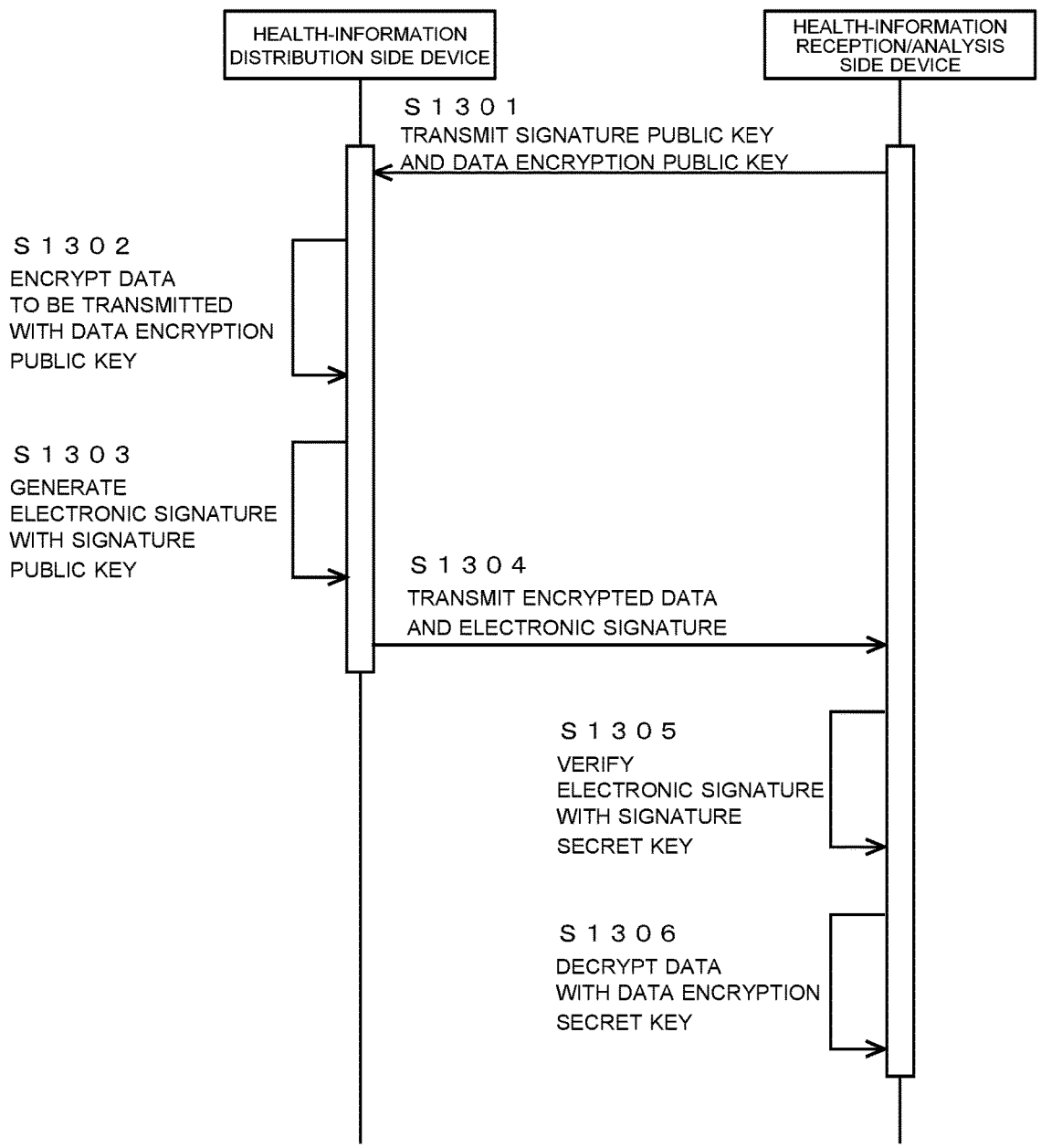
FIG. 18 is a sequence diagram showing an example of a flow of exchanging data between devices in third embodiment of the present invention.

Here, a procedure when data is exchanged between devices using the public key encryption method to encrypt data will be described. FIG. 18 shows the flow of a process in the case where data is transmitted from the health-information distribution side device 1 to a health-information reception/analysis side device 2a, as an example. Here, a case of adopting the public key encryption method to encrypt data will be exemplified.

First, in step S1301, a signature public key included in the signature key 2115 and a data encryption public key included in the data encryption key 2113 which are held by the health-information reception/analysis side device 2a are transmitted from the health-information reception/analysis side device 2a to the health-information distribution side device 1. This may be started as a process for requesting transmission of data from the health-information reception/analysis side device 2a to the health-information distribution side device 1, or as a response to a request of data accepting from the health-information distribution side device 1 to the health-information reception/analysis side device 2a.

In step S1302, the health-information distribution side device 1 performs a data encryption process with the data encryption public key received in step S1301. Then, in step S1303, an electronic signature for the encrypted data is generated using the signature public key received in step S1301. This process is, as described above with reference to steps S1003 to S1004 in FIG. 16A, to generate a hash value of the encrypted data and to encrypt it with the signature public key.

In step S1304, the data encrypted in step S1302 and the electronic signature generated in step S1303 are transmitted from the health-information distribution side device 1 to the health-information reception/analysis side device 2a.

When receiving the encrypted data and the electronic signature, the health-information reception/analysis side device 2a decrypts them. First, in step S1305, the electronic signature is verified. This process is, as described above with reference to steps S1101 to S1103 in FIG. 16B, to calculate a hash value of the encrypted data, decrypt the electronic signature using the electronic signature secret key held by itself, and compare the hash values obtained by those processes. Then, when it is determined that the data has not been altered by the verification of the electronic signature, the data is decrypted using the data encryption secret key held by itself in step S1306.

In this manner, by transmitting the public key used to encrypt a signature or data from a device that receives the data to a device that transmits the data, and performing a process for generating encrypted data or an electronic signature using the public key, it is possible only for the device that holds the secret key paired with each public key and receives the data to verify and decrypt the data.

When the common key encryption method is used to encrypt data, the data encryption key 2113 held by the health-information reception/analysis side device 2a is transmitted to the health-information distribution side device 1 in step S1301, and the data encryption key 2113 is used to perform the encryption in step S1302 and the decryption in step S1306.

Here, it has been exemplified that data is transmitted from the health-information distribution side device 1 to the health-information reception/analysis side device 2a, but when, for example, the data is analyzed in the health-information reception/analysis side device 2a, and the result is transmitted to the health-information distribution side device 1, a similar process is performed by exchanging the data transmission side and the reception side.

As described above, according to the system using the information management terminal device according to the present embodiment, by holding the signature key 1115 or 2115 as the alteration detection parameter in the concealed region, and performing the alteration detection process of data and a program using the electronic signature generated using the key, it is possible to use a recording medium in which the capacity of the concealed region is limited as the distribution side medium 11 or the reception/analysis side medium 21.

Furthermore, by preparing a signature key and a data encryption key which are different from each device, and transmitting the public key beforehand from the receiving side device to the transmitting side device at the time of transmitting and receiving data, it is possible to transmit and receive the data more safely in a state where verification and decryption can be performed only by the receiving side device of the data.

What is claimed is:

1. A system using an information management terminal device comprising:

a health information distribution side device implemented by using a distribution side medium implemented as a storage medium, and the health information distribution side device is the information management terminal device;

a health information reception/analysis side device; and a sensor configured to acquire first information, the first information being health information of a person which is an information owner, wherein the health information distribution side device comprising the distribution side medium, an encoder, and a distribution unit, wherein the distribution side medium includes:

a concealed region accessible by a specific program including a program causing the health information distribution side device to operate as the encoder and the distribution unit, the concealed region holds an alteration detection parameter for detecting alteration of the first information and/or second information and a data encryption key, and a normal region accessible also by programs other than the specific program, the normal region holds an electronic signature based on a hash value of the first information and the second information, the encoder:

acquires the first information from the sensor, sequentially stores, in the normal region, the first information and the second information without overwriting, the second information being additional information of the first information, adds a date/time record as the second information, and sequentially stores, in the normal region, the first information or a link capable of referring to the first information, and the second information or a link capable of referring to the second information, and the distribution unit:

generates a health information container to be distributed by selecting information to be distributed from the first information and the second information in the normal region and containerizing the first information and the second information, sets a concealment level which is designated by the information owner of the selected information to be distributed, wherein the concealment level is selected from one of the following:
  class 0 in which the information to be distributed is transmitted to the health information reception/analysis side device without being encrypted,
  class 1 in which the information to be distributed is encrypted and transmitted to the health information reception/analysis side device, and
  class 2 in which the information to be distributed is encrypted, prohibited from being copied at an output destination including the health information reception/analysis side device, set to have a validity period, and transmitted to the health information reception/analysis side device,
adds the concealment level to the information to be distributed as additional information, and
distributes the health information container and the electronic signature to the health information reception/analysis side device,
the health information reception/analysis side device comprising a reception/analysis side medium as a storage medium, a decoder, and a transmission/reception unit, wherein
the reception/analysis side medium includes:
  a concealed region accessible by a specific program including a program causing the health information reception/analysis side device to operate as the decoder and the transmission/reception unit, the concealed region holds a signature key and the data encryption key, and
  a normal region accessible also by programs other than the specific program,
the decoder analyzes or displays the first information and the second information according to the concealment level, and
the transmission/reception unit:
  receives the health information container and the electronic signature from the health information distribution side device through one-to-one communication by peer to peer (P2P) between the health-information distribution side device and the health-information reception/analysis side device,
  determines the concealment level added to the first information and the second information,
  detects whether the first information and/or the second information has been altered by verifying the electronic signature using the signature key, and
  handles the first information, the second information, and an analysis result according to the concealment level, in which
    for the class 0, the first information and the second information are handled without being encrypted,
    for the class 1, the first information and the second information are encrypted and handled, and
    for the class 2, the first information and the second information are encrypted, prohibited from being copied at the output destination, set to have a validity period, and handled.

2. The system using the information management terminal device according to claim 1, wherein the encoder performs an alteration detection process of the specific program using a program alteration detection parameter for detecting alteration of the specific program, the program alteration detection parameter being included in the concealed region.

3. The system using the information management terminal device according to claim 2, wherein the encoder periodically performs the alteration detection process of the specific program, and
the health information distribution side device deletes or recovers, when the encoder detects alteration of the specific program, the first information and the second information stored from a point of time when the alteration detection process of the specific program is previously performed until a point of time when the alteration of the specific program is detected.

4. The system using the information management terminal device according to claim 1, wherein
the encoder performs an alteration detection process of the first information and/or the second information using the alteration detection parameter, wherein
the health information distribution side device deletes or recovers, when the encoder detects alteration of the first information and/or the second information, the first information and the second information stored from a point of time when the alteration detection process of the first information and/or the second information is previously performed until a point of time when the alteration of the first information and/or the second information is detected.

5. The system for using the information management terminal device according to claim 1, wherein
the second information includes at least one of an output history of the distribution unit, information specifying an output destination of the distribution unit, the concealment level, and a process result at the output destination of the distribution unit.

6. The system using the information management terminal device according to claim 1, wherein
the health information distribution side device performs a biometric authentication of the information owner,
the encoder:
  acquires identifiers unique to the sensors to be targeted by the information owner when the sensor is installed, initially registered, or changed in the registration;
  stores the identifiers in the normal region;
  performs an authentication process of the sensor using the identifiers in the normal region;
  acquires the first information from the sensor when it is determined that the authentication process of the sensor succeeded.

7. The system using the information management terminal device according to claim 1, wherein
the first information includes biological information and behavior information,
the decoder performs analysis by visualizing mutual relations of the biological information, the behavior information, and environmental information.

8. The system using the information management terminal device according to claim 1, wherein
the decoder:
  reanalyzes the analysis result,
  transmits a second analysis result to the output destination,
the transmission/reception unit receives the analysis result from the output destination.

9. The system using the information management terminal device according to claim 1, wherein the health information reception/analysis side device is a second information management terminal device.

* * * * *